US009289415B2

(12) United States Patent
Shi et al.

(10) Patent No.: US 9,289,415 B2
(45) Date of Patent: Mar. 22, 2016

(54) TREATMENT OF CANCER

(75) Inventors: Yujiang Geno Shi, Chestnut Hill, MA (US); Christine Guo Lian, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/241,944

(22) PCT Filed: Sep. 4, 2012

(86) PCT No.: PCT/US2012/053605
§ 371 (c)(1),
(2), (4) Date: Mar. 6, 2014

(87) PCT Pub. No.: WO2013/033688
PCT Pub. Date: Mar. 7, 2013

(65) Prior Publication Data
US 2014/0206757 A1 Jul. 24, 2014

Related U.S. Application Data

(60) Provisional application No. 61/530,035, filed on Sep. 1, 2011.

(51) Int. Cl.
| *A61K 31/40* | (2006.01) |
| *A61K 31/404* | (2006.01) |
| *G01N 33/50* | (2006.01) |
| *A61K 45/06* | (2006.01) |
| *A61K 31/22* | (2006.01) |
| *A61K 31/351* | (2006.01) |
| *A61K 31/505* | (2006.01) |
| *A61K 31/366* | (2006.01) |
| *A61N 5/10* | (2006.01) |

(52) U.S. Cl.
CPC ............... *A61K 31/404* (2013.01); *A61K 31/22* (2013.01); *A61K 31/351* (2013.01); *A61K 31/366* (2013.01); *A61K 31/40* (2013.01); *A61K 31/505* (2013.01); *A61K 45/06* (2013.01); *A61N 5/10* (2013.01); *G01N 33/5011* (2013.01); *G01N 2333/90245* (2013.01)

(58) Field of Classification Search
USPC .................................................. 514/419, 460
See application file for complete search history.

(56) References Cited

U.S. PATENT DOCUMENTS

| 6,534,540 B2 * | 3/2003 | Kindness et al. | 514/461 |
| 2012/0053196 A1 * | 3/2012 | Jirstrom et al. | 514/277 |

FOREIGN PATENT DOCUMENTS

| WO | WO 2007/021839 A2 | 2/2007 |
| WO | WO2010043721 A1 | 4/2010 |
| WO | WO2011017583 A1 | 2/2011 |
| WO | WO2011035941 A1 | 3/2011 |

OTHER PUBLICATIONS

Fromigue et al., The Journal of Pharmacology and Experimental Therapeutics, 2008, 325(2): 595-600.*
Schmidmaier et al., European Journal of Haematology, 2007, 79(3): 240-243.*
Lokhorst et al. CAS: 2005: 479526, 2005.*
Barclay M. et al., Cancer 8(2):253-260 (Mar.-Apr. 1955). "Human plasma lipoproteins, I. In normal women and in women with advanced carcinoma of the breast."
Hayami, S. et al., Int J Cancer 128(3):574-586 (Feb. 1, 2011). doi: 10.1002/ijc.25349. "Overexpression of LSD1 contributes to human carcinogenesis through chromatin regulation in various cancers."
Heidenblad, M. et al., BMC Med Genomics 1:3 (Jan. 31, 2008). doi: 10.1186/1755-8794-1-3. "Tiling resolution array CGH and high density expression profiling of urothelial carcinomas delineate genomic amplicons and candidate target genes specific for advanced tumors."
Huang, J. et al., Nature 449(7158):105-8 (Sep. 6, 2007). "p53 is regulated by the lysine demethylase LSD1."
Huang Y. et al., Breast Cancer Res Treat. 131(3):777-789 (Feb. 2012). doi: 10.1007/s10549-011-1480-8. Epub Mar. 31, 2011. "Inhibitors of histone demethylation and histone deacetylation cooperate in regulating gene expression and inhibiting growth in human breast cancer cells."
Kaufman R.J. et al., Cancer 8(5):888-889 (Sep.-Oct. 1955). "Human plasma lipoproteins. II. The effect of osseous metastases in patients with advanced carcinoma of the breast."
Mahadevan N.R. et al., Proc Natl Acad Sci U.S.A. 108(16):6561-6566 Apr. 19, 2011. doi: 10.1073/pnas.1008942108. Epub Apr. 4, 2011. "Transmission of endoplasmic reticulum stress and pro-inflammation from tumor cells to myeloid cells."
Orlic, M. et al., Genes Chromosomes Cancer. 45(1):72-82 (Jan. 2006). "Expression analysis of 6p22 genomic gain in retinoblastoma."
Ross J.S. et al., Ann N.Y. Acad Sci. 947:271-292; discussion 292-293 (Dec. 2001). "Atherosclerosis and cancer: common molecular pathways of disease development and progression."
Singh, M.M. et al., Neuro Oncol. 13(8):894-903 (Aug. 2011). doi: 10.1093/neuonc/nor049. Epub Jun. 8, 2011. "Inhibition of LSD1 sensitizes glioblastoma cells to histone deacetylase inhibitors."
Binda, C. et al., J Am Chem Soc.132(19):6827-6833 (May 19, 2010). doi: 10.1021/ja101557k. "Biochemical, structural, and biological evaluation of tranylcypromine derivatives as inhibitors of histone demethylases LSD1 and LSD2."
Cain, C., SciBX 5(14):1-3; doi:10.1038/scibx.2012.352, published online Apr. 5, 2012. "AML takes LSD1."
Feleszko, W. et al., Int J Cancer. 100(1):111-118 (Jul. 1, 2002). "Lovastatin potentiates antitumor activity of doxorubicin in murine melanoma via an apoptosis-dependent mechanism."

(Continued)

*Primary Examiner* — Rei-Tsang Shiao
(74) *Attorney, Agent, or Firm* — Nixon Peabody LLP; David S. Resnick; Tari W. Mills

(57) ABSTRACT

This disclosure provides agents, compositions and methods of treating cancer by inhibiting histone lysine specific demethylase 1 (LSD1) and/or and a histone lysine specific demethylase 2 (LSD2). Agents and compositions comprise statins and/or inhibitors of LSD1/2.

5 Claims, 16 Drawing Sheets

(56) References Cited

OTHER PUBLICATIONS

Gao, J. et al., Zhonghua Gan Zang Bing Za Zhi 18(12):900-904 (Dec. 2010). doi: 10.3760/cma.j.issn.1007-3418.2010.12.005. "Effects of celecoxib combined with fluvastatin on tumor growth and cell apoptosis in a xenograft model of hepatocellular carcinoma."

Lin, Y. et al., Cancer Res. 68(7):2375-2383 (Apr. 1, 2008). doi: 10.1158/0008-5472.CAN-07-5807. "Statins increase p21 through inhibition of histone deacetylase activity and release of promoter-associated HDAC1/2."

Schmidmaier, R. et al., Eur J Haematol. 79(3):240-243 (Sep. 2007). Epub Jul. 26, 2007. "First clinical experience with simvastatin to overcome drug resistance in refractory multiple myeloma."

Shibata, M., Carcinogenesis (10):1887-1898 (Oct. 25, 2004). Epub Jun. 3, 2004. "Lovastatin inhibits tumor growth and lung metastasis in mouse mammary carcinoma model: a p53-independent mitochondrial-mediated apoptotic mechanism."

Soma, M.R. et al., Cancer Res. 55(3):597-602 (Feb. 1, 1995). "In vivo enhanced antitumor activity of carmustine [N,N'-bis(2-chloroethyl)-N-nitrosourea] by simvastatin."

* cited by examiner

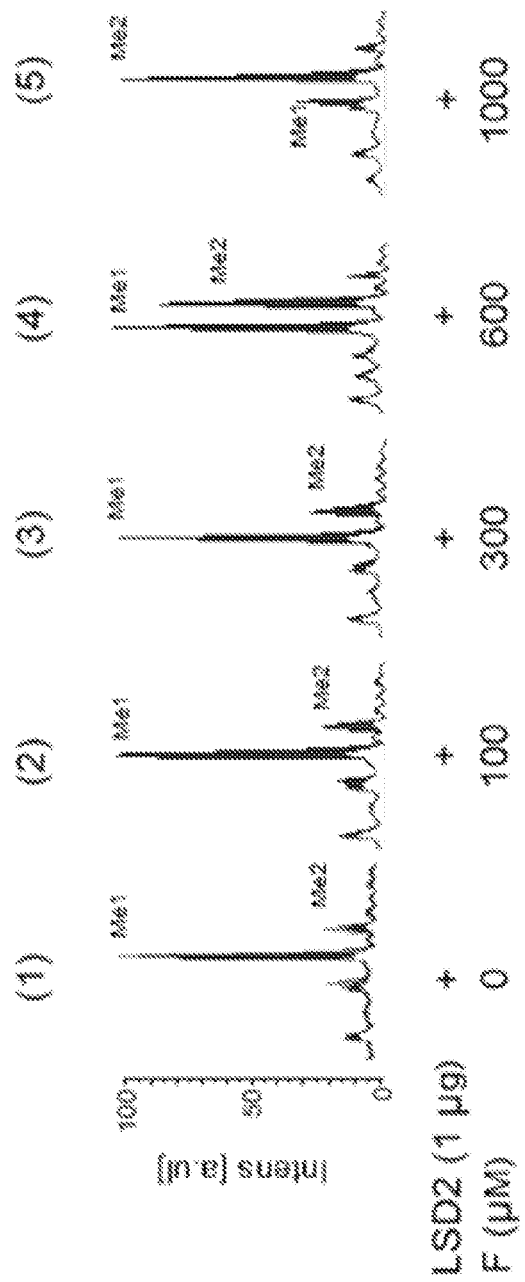
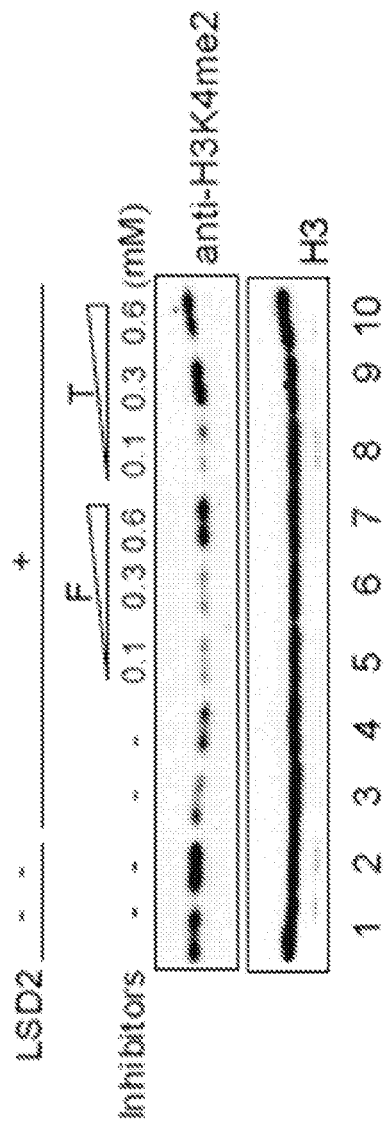
FIG. 5B
FIG. 5C

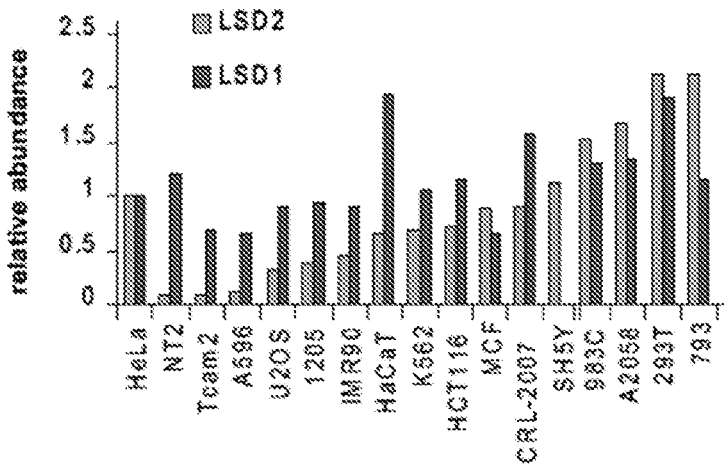

| Relative | cell line | description |
|---|---|---|
| 1 | HeLa | cervical carcinoma |
| 0.10 | NT-2 | embryonic carcinoma |
| 0.10 | Tcam-2 | seminoma |
| 0.13 | A596 | carcinomic human alveolar basal epithelial |
| 0.33 | U2OS | osteosarcoma |
| 0.40 | 1205 | metastatic melanoma, p52 mutant |
| 0.46 | IMR90 | embryonic lung fibroblast, normal diploid |
| 0.68 | HaCaT | human keratinocyte cell line |
| 0.71 | K562 | myelogenous leukemia cell line |
| 0.72 | HCT116 | human colon carcinoma |
| 0.88 | MCF | breast adenocarcinoma |
| 0.90 | CRL-2007 | normal testis fibroblast |
| 1.13 | SH5Y | neuroblastoma |
| 1.53 | 983C | metastatic carcinoma, p10 mutant |
| 1.66 | A2058 | metastatic melanoma |
| 2.11 | 293T | embryonic kidney |
| 2.13 | 793 | primary melanoma, p58 mutant |

*FIG. 9*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtgtttcaa ggctacagca                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctctagcctc ccaaccttcc                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgggttttag gaccaggatg                                                      20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtgctgaag ctggcagt                                                        18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtgcgtgtc cagaagattg                                                      20
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtgatccct tccgtccttg                                             20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatgaggatg atgaaaatgg c                                           21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctaattttct aatagggttg aaggg                                       25
```

TREATMENT OF CANCER

CROSS REFERENCE TO RELATED APPLICATIONS

This application is a 35 U.S.C. 371 National Stage Application of International Application No. PCT/US2012/053605 filed on Sep. 4, 2012, which designates the United States, and which claims benefit under 35 U.S.C. §119(e) of U.S. Provisional Application No. 61/530,035 filed Sep. 1, 2011, the contents of each of which are incorporated herein by reference in its entirety.

GOVERNMENT SUPPORT

This invention was made with Government support under Grant Nos.: R01DK077036 and R01GM78458 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 7, 2014, is named 20140307_SequenceListing_TextFile_043214-071632-US and is 2,120 bytes in size.

FIELD

This invention relate to cancer therapeutics and new use of cholesterol lowing drugs for the treatment of cancer.

BACKGROUND

Despite years of research into the development of new methods of treatment, many types of cancer, including, e.g., breast and colon cancer, remain quite common. Continued search and development of more anti-cancer agents to complement or replace existing treatments is clearly desired.

SUMMARY

Embodiments of this disclosure are based on the discovery that cholesterol-lowering drugs, statins, have epigenetic modulating adjuvant activities, thereby epigenetically altering the regulation of expression of genes in chromosomes. Specifically, statins inhibit histone lysine specific demethylase 1 (LSD1) and/or and a histone lysine specific demethylase 2 (LSD2) and bring forth cell death in the human cancer cell. Inhibiting LSD1 and 2 activities specifically affect the methylation states of genes encompassed in chromatins; the methylation level of genes is increased, which leads to alter gene expression. The cell death, apoptosis, which is induced by statins, is not mitigated by mevalonate. Accordingly, inhibiting the activities of LSD1 and/or LSD2 can be used to induce apoptosis when desired, for example, in cancer and tumor treatment, when there is a desire to kill all cancer cells so as not to select for resistant cancer cells during typical cancer chemotherapy.

Accordingly, in one embodiment, it is the objective of this disclosure to provide additional cancer therapeutics to the existing repertoire of cancer therapies currently available.

In another embodiment, it is also the objective of this disclosure to provide a new use of cholesterol-lowering drugs, e.g., for cancer treatment.

In another embodiment, it is also the objective of this disclosure to provide a new therapeutic to be used in conjunction with existing repertoire of cancer therapies for the prevention of development of chemotherapy resistance cancer.

In one embodiment, the disclosure herein provides a method for treating cancer in a subject comprising administering to a subject in need thereof a therapeutically effective amount of an epigenetic modulating adjuvant agent in conjunction with at least one chemotherapy, wherein the epigenetic modulating adjuvant agent promotes chemo-protection and reducing chemo-resistance. In one embodiment, the epigenetic modulating adjuvant agent enhance the drug efficacy of the at least one chemotherapy to promotes chemo-protection and reducing the development of chemo-resistance cancer cells in the subject.

In one embodiment, the disclosure herein provides a method for enhancing the drug efficacy of at least one cancer chemotherapy in a subject to promote chemo-protection and reducing the development of chemo-resistance cancer cells in the subject comprising administering to the subject in need thereof a therapeutically effective amount of at least one an epigenetic modulating adjuvant agent in conjunction with the at least one chemotherapy.

In one embodiment, the disclosure herein provides a method for treating chemotherapy resistant cancer in a subject, the method comprising determining whether chemotherapy resistant cancer cell population of the subject are susceptible to an epigenetic modulating adjuvant agent; and, if so, administering to the subject a therapeutically effective amount of the epigenetic modulating agents, wherein the agent treats chemotherapy resistant cancer in the subject by inducing apoptosis of the chemotherapy resistant cancer cells, and wherein the apoptosis induced is at least 10% compared to cancer cells of the subject in the absence of the epigenetic modulating adjuvant agent.

In one embodiment, the epigenetic modulating adjuvant agent is an inhibitor of a histone demethylase, (e.g., histone lysine specific demethylase 1 (LSD1) and/or and a histone lysine specific demethylase 2 (LSD2). In one embodiment, the at least one chemotherapy is an alkylating chemotherapeutic drug. In one embodiment, the alkylating chemotherapeutic drug is an alkylating antineoplastic agent. In one embodiment, the alkylating antineoplastic agent attaches an alkyl group ($C_nH_{2n+1}$) to DNA.

In one embodiment, the epigenetic modulating adjuvant agent enhance the drug efficacy of the at least one chemotherapy to promotes chemo-protection and reducing the development of chemo-resistance cancer cells in the subject. In one embodiment, the enhancement of the chemo drug efficacy is at least 10% over a control level.

In one embodiment, the disclosure herein provides a method for treating cancer in a subject comprising administering to a subject in need thereof a therapeutically effective amount of an inhibitor of a histone lysine specific demethylase 1 (LSD1) and/or and a histone lysine specific demethylase 2 (LSD2).

In one embodiment, the disclosure herein provides a method for treating cancer in a subject comprising administering to a subject in need thereof a composition comprising an inhibitor of LSD1 and/or and a LSD2.

In another embodiment, the disclosure herein provides a method for treating cancer in a subject, the method comprising administering to the subject a therapeutically effective amount of an inhibitor of LSD1 and/or LSD2, wherein cancer cells of the subject has been determined to be susceptible to apoptosis induced by the inhibitor of LSD1 and/or LSD2.

In another embodiment, the disclosure herein provides a method for treating cancer in a subject, the method comprising administering to the subject a composition comprising an inhibitor of LSD1 and/or LSD2, wherein cancer cells of the subject has been determined to be susceptible to apoptosis induced by the inhibitor of LSD1 and/or LSD2.

In another embodiment, the disclosure herein provides a method for treating cancer in a subject, the method comprising first determining whether cancer cells of the subject are susceptible to apoptosis induced by an inhibitor of LSD1 and/or LSD2; and, if so, administering to the subject a therapeutically effective amount of the inhibitor of LSD1 and/or LSD2, wherein the inhibitor treats cancer in the subject.

In another embodiment, the disclosure herein provides a method for treating cancer in a subject, the method comprising first determining whether cancer cells of the subject are susceptible to apoptosis induced by an inhibitor of LSD1 and/or LSD2; and, if so, administering to the subject a composition comprising the inhibitor of LSD1 and/or LSD2, wherein the inhibitor treats cancer in the subject.

In one embodiment of any method described herein, the inhibitor of LSD1 and/or LSD2 induces apoptosis in the cancer cells of the subject.

In one embodiment of any method described herein, the apoptosis induced is at least 10% increase compared to cancer cells of the subject in the absence of the inhibitor of LSD1 and/or LSD2. That is the inhibitor of LSD1 and/or LSD2 should induce more apoptosis is the experimented cancer cells (in the presence of the inhibitor) than in the control cancer cells (in the absence of the inhibitor).

In one embodiment, the disclosure herein provides a method for treating cancer in a subject comprising administering to a subject in need thereof a therapeutically effective amount of a statin.

In one embodiment, the disclosure herein provides a method for treating cancer in a subject comprising administering to a subject in need thereof a composition comprising a statin.

In another embodiment, the disclosure herein provides a method for treating cancer in a subject, the method comprising administering to the subject a therapeutically effective amount of a statin, wherein cancer cells of the subject has been determined to be susceptible to apoptosis induced by the statin.

In another embodiment, the disclosure herein provides a method for treating cancer in a subject, the method comprising administering to the subject a composition comprising a statin, wherein cancer cells of the subject has been determined to be susceptible to apoptosis induced by the statin.

In another embodiment, the disclosure herein provides a method for treating cancer in a subject, the method comprising first determining whether cancer cells of the subject are susceptible to apoptosis induced by a statin; and, if so, administering to the subject a therapeutically effective amount of the statin, wherein the statin treats cancer in the subject.

In another embodiment, the disclosure herein provides a method for treating cancer in a subject, the method comprising first determining whether cancer cells of the subject are susceptible to apoptosis induced by a statin; and, if so, administering to the subject a composition comprising the statin, wherein the statin treats cancer in the subject.

In one embodiment of any method described herein, the statin induces apoptosis in the cancer cells of the subject.

In one embodiment of any method described herein, the apoptosis induced is at least 10% compared to cancer cells of the subject in the absence of statin.

In one embodiment of any method described herein, the apoptosis is measured by any method known in the art. In another embodiment of any method described herein, the apoptosis is measured by a method selected from the group consisting of a cell free apoptotic assay, a DNA fragmentation assay, a DNA laddering assay, an annexin V staining assay and a terminal transferase dUTP nick end Labeling (TUNEL) assay.

In one embodiment of any method described herein, the inhibitor of LSD1 and/or LSD2 is a statin. In another embodiment of any method described herein, the wherein the inhibitor of a LSD1 and/or and a LSD2 is not a statin.

In one embodiment of any method described herein, the statin is selected from the group consisting of fluvastatin, lovastatin, simvastatin, mevastatin, pravastatin, atorvastatin, and rosuvastatin. In one embodiment of any method described herein, the statin is fluvastatin.

In one embodiment of any method described herein, a combination of more than one statin is administered or included in the composition administered for cancer therapy. For example, fluvastatin and atorvastatin.

In one embodiment of any method described herein, the inhibitor of LSD1 and/or LSD2 is a monoamine oxidase inhibitor.

In one embodiment of any method described herein, the monoamine oxidase inhibitor is tranylcypromine, derivatives or analogues thereof.

In one embodiment of any method described herein, the inhibitor of LSD1 and/or LSD2 is selected from the group consisting of safrazine, parygline, nialamide, mebanazine, isocarboxazid, iprocozide, clorygline, cimoxatone, and beflomatone.

In one embodiment of any method described herein, the inhibitor of LSD1 and/or LSD2 is a compound selected from the group consisting of the phenylcyclopropylamine derivatives of WO 2010143582 and the cyclopropylamine derivatives of WO 2012013727.

In one embodiment of any method described herein, the inhibitor of LSD1 and/or LSD2, or statin is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment of any method described herein, the composition comprising an inhibitor of LSD1 and/or LSD2, or statin is formulated to be administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment of any method described herein, the inhibitor of LSD1 and/or LSD2 is administered in conjunction with at least one additional cancer therapy to achieve a combination cancer therapy.

In one embodiment of any method described herein, the statin is administered in conjunction with at least one additional cancer therapy to achieve a combination cancer therapy.

In one embodiment of any method described herein, the composition comprising an inhibitor of LSD1 and/or LSD2 is administered in conjunction with at least one additional cancer therapeutic to achieve a combination cancer therapy.

In one embodiment of any method described herein, the composition comprising a statin is administered in conjunction with at least one additional cancer therapeutic to achieve a combination cancer therapy.

In one embodiment of any method described herein, the composition comprising an inhibitor of LSD1 and/or LSD2 further comprises at least one additional cancer therapeutic.

In one embodiment of any method described herein, the composition comprising a statin further comprises at least one additional cancer therapeutic.

In one embodiment of any method described herein, wherein the at least one additional cancer therapy is selected from the group consisting of surgery, radiation therapy, chemotherapy, immunotherapy and gene therapy.

In one embodiment of any method described herein, wherein the subject is a mammal. In another embodiment, the subject is a primate mammal. In other embodiment, the subject is human.

In one embodiment of any method described herein, the inhibitor of LSD1 and/or LSD2, or statin, or the composition further comprises a pharmaceutically acceptable carrier.

In one embodiment of any method described herein, the method further comprises selecting a subject who has cancer or has been diagnose with cancer.

In one embodiment, the disclosure described herein provides a composition comprising at least one inhibitor of a LSD1 and/or and a LSD2, and a pharmaceutically acceptable carrier.

In one embodiment, the disclosure described herein provides a composition comprising at least one inhibitor of a LSD1 and/or and a LSD2, at least one additional cancer therapeutic and a pharmaceutically acceptable carrier.

In one embodiment, the disclosure described herein provides a composition comprising at least one inhibitor of a LSD1 and/or and a LSD2, at least a statin, and a pharmaceutically acceptable carrier, wherein the inhibitor of a LSD1 and/or and a LSD2 is not a statin.

In one embodiment, the disclosure described herein provides a composition comprising at least one inhibitor of a LSD1 and/or and a LSD2, at least a statin, at least one additional cancer therapeutic and a pharmaceutically acceptable carrier, wherein the inhibitor of a LSD1 and/or and a LSD2 is not a statin.

In one embodiment, the disclosure described herein provides a composition comprising at least one statin, at least one additional cancer therapeutic and a pharmaceutically acceptable carrier.

In one embodiment of any composition described herein, the composition is used for the treatment of cancer.

In one embodiment, the disclosure described herein provides an inhibitor of a LSD1 and/or and a LSD2 for use in the treatment of cancer.

In one embodiment, the disclosure described herein provides an inhibitor of a LSD1 and/or and a LSD2 and at least one additional cancer therapeutic for use in the treatment of cancer.

In one embodiment, the inhibitor of LSD1 and/or LSD2 is a statin.

In one embodiment, the disclosure described herein provides a statin for use in the treatment of cancer in a subject.

In one embodiment, the disclosure described herein provides an inhibitor of a LSD1 and/or and a LSD2 and a statin for use in the treatment of cancer, wherein the inhibitor of a LSD1 and/or and a LSD2 is not a statin.

In one embodiment, the disclosure described herein provides an inhibitor of a LSD1 and/or and a LSD2, a statin and at least one additional cancer therapeutic for use in the treatment of cancer, wherein the inhibitor of a LSD1 and/or and a LSD2 is not a statin.

In one embodiment, the statin is selected from the group consisting of fluvastatin, lovastatin, simvastatin, mevastatin, pravastatin, atorvastatin, and rosuvastatin.

In one embodiment, the statin is fluvastatin.

In one embodiment, the inhibitor of LSD1 and/or LSD2 is a monoamine oxidase inhibitor.

In one embodiment, the monoamine oxidase inhibitor is tranylcypromine derivatives or analogues thereof.

In one embodiment, the inhibitor of LSD1 and/or LSD2 is selected from the group consisting of safrazine, parygline, nialamide, mebanazine, isocarboxazid, iprocozide, clorygline, cimoxatone, and beflomatone.

In one embodiment, the inhibitor of LSD1 and/or LSD2 is a compound selected from the group consisting of the phenylcyclopropylamine derivatives of WO 2010143582 and the cyclopropylamine derivatives of WO 2012013727.

In one embodiment, the inhibitor of LSD1 and/or LSD2, or statin is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment, the inhibitor of LSD1 and/or LSD2, or statin is administered in conjunction with at least one additional cancer therapy to achieve a combination cancer therapy.

In one embodiment of any of the composition described herein, the composition is formulated to be administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment of any of the composition described herein, the composition is administered in conjunction with at least one additional cancer therapy to achieve a combination cancer therapy.

DEFINITIONS

As used herein, the term "comprising" or "comprises" is used in reference to methods, and respective component(s) thereof, that are essential to the claims, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

As used herein, the term "an epigenetic modulating adjuvant agent" refers to an agent that directly or indirectly changes the local environmental factors on genes in chromosomes and chromatin, and thereby alters the way the genes are expressed. As a result of its epigenetic effects on gene expression, the agent synergistically enhances the cytotoxic/apoptotic effects of chemotherapy drugs. For example, an epigenetic modulating adjuvant agent is a statin that indirectly changes the methylation on LSD1 and LSD2 mediated gene expression.

As used herein, the term "enhance drug efficacy" with reference to an epigenetic modulating adjuvant agent or a statin or an inhibitor of LSD1 and/or LSD2 refers to the agent/inhibitor/statin synergistically increasing the desired therapeutic effects of the drug. Wherein the drug is a chemotherapy drug with cytotoxic/apoptotic effects, the agent/inhibitor/statin would increase the cytotoxic/apoptotic effects of the chemotherapy drug. In one embodiment, the increase is at least 5% over the drug efficacy or cytotoxic/apoptotic effects of the drug noted in the absence of the epigenetic modulating adjuvant agent or a statin or an inhibitor of LSD1 and/or LSD2. In one embodiment, the "enhance drug efficacy" would mean that less chemotherapy drug would need to be administered to the subject. In one embodiment, the "enhance drug efficacy" would mean that the subject would experience less toxic side effects of the drug with the administration of a less amount of the drug.

As used herein, the term "promotes chemo-protection and reducing chemo-resistance" with reference to an epigenetic modulating adjuvant agent or a statin or an inhibitor of LSD1 and/or LSD2 refers to the decrease development of chemotherapy-resistant cancer cells in a subject after treatment with a full cycle or course of cancer chemotherapy. The decrease is at least 10% less chemotherapy-resistant cancer cells compared to in the absence of the epigenetic modulating adjuvant agent or a statin or an inhibitor of LSD1 and/or LSD2 during a similar course of cancer chemotherapy. In one embodiment, "promotes chemo-protection and reducing chemo-resistance" can refer to an increase in the time before the subject relapses again after a full cycle or course of cancer chemotherapy. The increase is at least 10% longer amount of time before symptoms indicating a cancer relapse in the subject compared to in the absence of the epigenetic modulating adjuvant agent or a statin or an inhibitor of LSD1 and/or LSD2 during a similar course of cancer chemotherapy.

As used herein, the term "chemotherapy resistant cancer" or "chemotherapy resistant cancer cell population" refers to cancer in a subject who has relapse after at least one full cycle or course of cancer chemotherapy.

As used herein, the term "apoptosis" refers to a natural process of self-destruction in certain cells that is determined by the genes and can be initiated by a stimulus or by removal of a repressor agent, e.g., an inhibitor of LSD1 and/or LSD2. "Apoptosis" is also known as programmed cell death. Several biochemical events lead to characteristic cell changes (morphology) and death. These changes include but are not limited to cell blebbing, cell shrinkage, nuclear fragmentation, chromatin condensation, and chromosomal DNA fragmentation. Analysis of apoptosis can be performed by any method known in the art and as described in the Example Section, non-limiting examples include cell free apoptotic assay, DNA fragmentation assay, DNA laddering assay, terminal transferase dUTP nick end labeling (TUNEL) assay and Annexin A5 (or annexin V) detection. The DNA can be labeled with propidium iodide or 7-AAD and analysed by flow cytometry.

As used herein, in one embodiment, the term "an inhibitor of LSD1 and/or a LSD2" refers to any molecule that inhibits the enzymatic activity of LSD1 and/or and a LSD2. In one embodiment, the enzymatic activity of LSD1/2 is the demethylation of mono- and di-methylated lysines, specifically histone 3, lysines 4 and 9 (H3K4 and H3K9). Analysis of the enzymatic activity of LSD1/2 and an inhibitor of such activity can be assayed by any method known in the art, including the method described in the Example Section. For example, the method described by Y. Tsukada and K. I. Nakayama, Cold Spring Harb. Protoc. 2010, protocol #5512; and by using the LSD1 Inhibitor Screening Assay Kit for Lysine-Specific Demethylase 1 by Cayman Chemical catalog #700120.

As used herein, the term "inhibit" or "inhibition" with respect to an inhibitor of LSD1 and/or and a LSD2 means the reduction or prevention of demethylation of mono- and di-methylated lysines by LSD1/2. Inhibition includes slowing the rate of non-methylated or mono-methylated enzymatic end-products. The reduction can by about 20%, about 30%, about 40%, about 50%, about 60%, about 70%, about 80%, about 90%, about 100% compared to a control which is an assay conducted in the absence of the inhibitor.

As used herein, the term "statin" refers to any of a class of lipid-lowering drugs that reduce serum cholesterol levels by inhibiting HMG-CoA reductase, a key enzyme involved in the biosynthesis of cholesterol, the mevalonate pathway or HMG-CoA reductase pathway. Non-limiting examples include fluvastatin, lovastatin, simvastatin, mevastatin, pravastatin, atorvastatin, and rosuvastatin.

A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "cancer therapy" refers to a therapy useful in treating cancer. Examples of anti-cancer therapeutic agents include, but are not limited to, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

In one embodiment, "administration" and "treatment," as it applies to a subject, refers to the contact of an exogenous pharmaceutical, therapeutic, or composition to the subject. In another embodiment, "administration" and "treatment," as it applies to a subject, refers to the contact of an inhibitor of LSD1 and/or and a LSD2, or a statin to the subject.

In one embodiment, as used herein, the term "treat' or treatment" refers to reducing or alleviating at least one adverse clinical symptom associated with cancer, e.g., pain, swelling, low blood count etc. In another embodiment, the term "treat' or treatment" refers to slowing or reversing the progression neoplastic uncontrolled cell multiplication, i.e. shrinking existing tumors and/or halting tumor growth. In another embodiment, the term "treat' or treatment" refers to inducing apoptosis in cancer or tumor cells in the subject.

As used herein, the term "a therapeutically effective amount" refers to an amount sufficient to achieve the intended purpose of treating cancer. In one embodiment, a therapeutically effective amount of an inhibitor of LSD1 and/or and a LSD2, or a statin or a composition described herein for a method of treating cancer is an amount of sufficient to induce apoptosis of cancer cells of the subject as compared to in the absent of the inhibitor of LSD1 and/or and a LSD2, or a statin or a composition respectively. In other embodiments, the amount that is safe and sufficient to treat, delay the development of a tumor, and/or delay further growth of the tumor. In some embodiments, the amount can thus cure or result in amelioration of the symptoms of cancer and tumor growth, slow the course of cancer progression, slow or inhibit a symptom of cancer, slow or inhibit the establishment of secondary symptoms of cancer or inhibit the development of a secondary symptom of the cancer. For example, an effective amount of an inhibitor of LSD1 and/or and a LSD2, or a statin or a composition described herein can inhibits tumor further growth, cause a reduction in size or even completely halt tumor growth, shrink the sizes of tumor, even complete regression of tumor, and reduce clinical symptoms associated with tumor. An effective amount for treating cancer is an amount of an inhibitor of LSD1 and/or and a LSD2, or a statin or a composition described herein sufficient to result in a reduction or complete removal of the symptoms of the disorder, disease, or medical condition. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount". However, for any given case, an appropriate "effective amount" can be determined by a skilled artisan according to established methods in the art using only routine experimentation.

BRIEF DESCRIPTION OF THE DRAWINGS

FIG. 3A shows the LSD1 demethylase assays on bulk histones. Bulk histones were incubated in the absence (−, lanes 1) or presence (+, lanes 2-8) of purified recombinant LSD1 (rLSD1) with increasing amounts of fluvastatin (F, lanes 3-5) or tranylcypromine (T, lanes 6-8). H3K4Me2 levels were detected with methyl-specific antibody (upper panel) and total H3 detected by pan-H3 antibody (lower panel) to demonstrate equal loading.

FIG. 3B shows the LSD1 demethylase assays on nucleosomes. Purified nucleosomes were incubated in the absence (−, lanes 1) or presence (+, lanes 2-6) of endogenous LSD1 (purified from HeLa cells as part of a CtBP complex). Reactions were performed with increasing amounts of fluvastatin (lanes 3-6). Di-methyl H3K4 and total H3 was detected as described in (A).

FIG. 4A shows the LSD1 and H3K4Me2 levels at the promoters of SCN2A and Syn1.1. HeLa cells were treated with 10 µmol/L fluvastatin (white bar) or vehicle control (black bar) for 72 hours. ChIP assays were performed using anti-H3K4Me2, anti-LSD1, or control rabbit IgG followed by detection of SCN2A (left panel) and SYN1.1 (right panel) promoter regions by quantitative real-time PCR. Note: fluvastatin does not inhibit promoter binding of LSD1.

FIG. 4B shows that statins de-repress LSD1-mediated gene repression. HeLa cells were treated for 72 hours with increasing amounts of statins (ranging from concentrations of 0, 2, 5 and 10 μmol/L. SCN2A (left panel) and SYN1.1 (right panel) gene expression was detected by quantitative real-time RT-PCR. Fluvastatin (square); lovastatin (circle); simvastatin (diamond); pravastatin (star).

FIG. 4C shows that LSD1 overexpression can rescue statin de-repression of target genes. HeLa cells were incubated for 72 hours with 10 μmol/L of fluvastatin (F), lovastatin (L), or pravastatin (P). MOCK, mock-transfected HeLa (white bars); MOCK+statin, mock HeLa cells plus statins (grey bars); FgLSD1+statin, Flag-LSD1 overexpressing cells plus statins (black bars). Messenger RNA levels of SYN1.1 (left panel) and IL-6 (right panel) were detected by quantitative real-time RT-PCR.

FIG. 4D shows that mevalonate does not suppress the statin de-repression of target gene expression, SYN1.1 and IL-6, in Hela cells. HeLa cells were treated with fluvastatin or lovastatin with or without mevalonate for 72 hours with the concentrations of 10 μmol/L. No significant changes were detected of IL-6 (right panel) and SCN2A (left panel) gene expression of the groups with mevalonate treatment comparing to the group without mevalonate treatment by quantitative real-time RT-PCR.

FIGS. 5A-5C show that statins inhibits LSD2 demethylase activity.

FIG. 5A shows that statins inhibit LSD2 demethylase activity on H3K4Me2. Mass spectrometry analysis of demethylation assays. H3K4Me2 peptides alone (panel 1) demonstrate a major peak at a molecular mass of 2863 Dalton (Da) as previously reported. Peptide was incubated with purified LSD2 (panel 2), or various statin compounds (panels 3-8). The decrease in dimethylated peptide (Me2) and appearance of mono-methylated (Me1) peptide at a molecular mass of 2849 is indicated. T, tranylcypromine; F, fluvastatin; L, lovastatin; S, simvastatin; M, mevastatin; P, pravastatin. Note: effectiveness of LSD1 inhibition is S>L>F>M>P.

FIG. 5B shows the dose-dependent effect of fluvastatin on inhibition of LSD2 activity. Fluvastatin inhibits LSD2 activity in peptide demethylases assays in a dose-dependent manner. H3K4Me2 peptides were incubated with LSD2 alone (panel 1) or LSD2 plus increasing concentrations of fluvastatin (F) (panels 2-5).

FIG. 5C shows the LSD2 demethylase assays on bulk histones. Bulk histones were incubated in the absence (−, lanes 1 and 2) or presence (+, lanes 3-8) of purified recombinant LSD2 (rLSD2) with increasing amounts of fluvastatin (F, lanes 5-7) or tranylcypromine (T, lanes 8-10). H3K4Me2 levels were detected with methyl-specific antibody (upper panel) and total H3 detected by pan-H3 antibody (lower panel) to demonstrate equal loading.

FIG. 6A that a subset of statins induces cell death in Hela cells. HeLa cells were treated with control, fluvastatin, lovastatin or pravastatin 0, 1.25, 2.5, 5 or 10 μmol/L for 24 hours. Up to 70% cell death was observed by fluvastatin and lovastatin. No significant cell death was induced by pravastatin at the same dose.

FIG. 6B shows that LSDs overexpression can rescue statin induced apoptotic cells in Hela cells. Suspension Hela cell (POZ) were treated with control, fluvastatin, lovastatin or provastatin 0, 1.25, 2.5, 5 or 10 μmol/L for 24 hours. Apoptotic cell populations as "sub-G1" peak were detected by Flow Cytometry in mock control and ΔLSD1 control groups, while no apoptotic cells were detected in control group and pravastatin treated group. In the Hela cells with overexpression of LSD1 or LSD2, the percentage of sub-G1 peak were significantly reduced comparing to the mock or ΔLSD1 (mutated LSD1 in vector with no LSD1 activity) control groups. Representative Flow Cytometry represents the results of at least three independent experiments of HeLa cells. MOCK—transfected HeLa, ΔLSD1-transfected Hela, LS1 or LSD2 over-expressed Hela cell groups were treated for 24 hours with 10 μmol/L or 20 μmol/L of fluvastatin (F), lovastatin (L), or simvastatin (S). Percentage of sub-G1 apoptotic cells were significantly decreased in LSDs over-expressed groups comparing to the two control groups. Representative histograph represents the results of at least three independent experiments.

FIG. 6C shows that mevelonic cannot rescue statin induced cell death in Hela cancer cells.

FIGS. 7A-7B show the catalytic site of LSD1 and the positioning of a peptide and FAD co-factor.

FIG. 7C shows the chemical structure of fluvastatin.

FIGS. 7D-7F show the docking model of fluvastatin in the LSD1 active site. Frontal view of the molecular surface of the LSD1 catalytic pocket containing fluvastatin as predicted by docking model. Positive and negative electrostatic residues of the LSD1 active site are indicated. Fluvastatin molecule (insert A') is represented by a stick model. The potential molecular and structural mechanism for statin inhibition of LSDs catalytic activity. Back view of a fluvastatin-containing LSDs' catalytic pocket is shown superimposed with FAD co-factor as well as H3K4Me2 peptide. Surface charges of LSD1 catalytic pocket are as described above. Arrow indicates a stereo picture of H3K4Me2 peptide in space filling format.

FIG. 9 show the relative abundance of LSD1 and LSD2 in various human cancers.

DETAILED DESCRIPTION

Figure 1A:
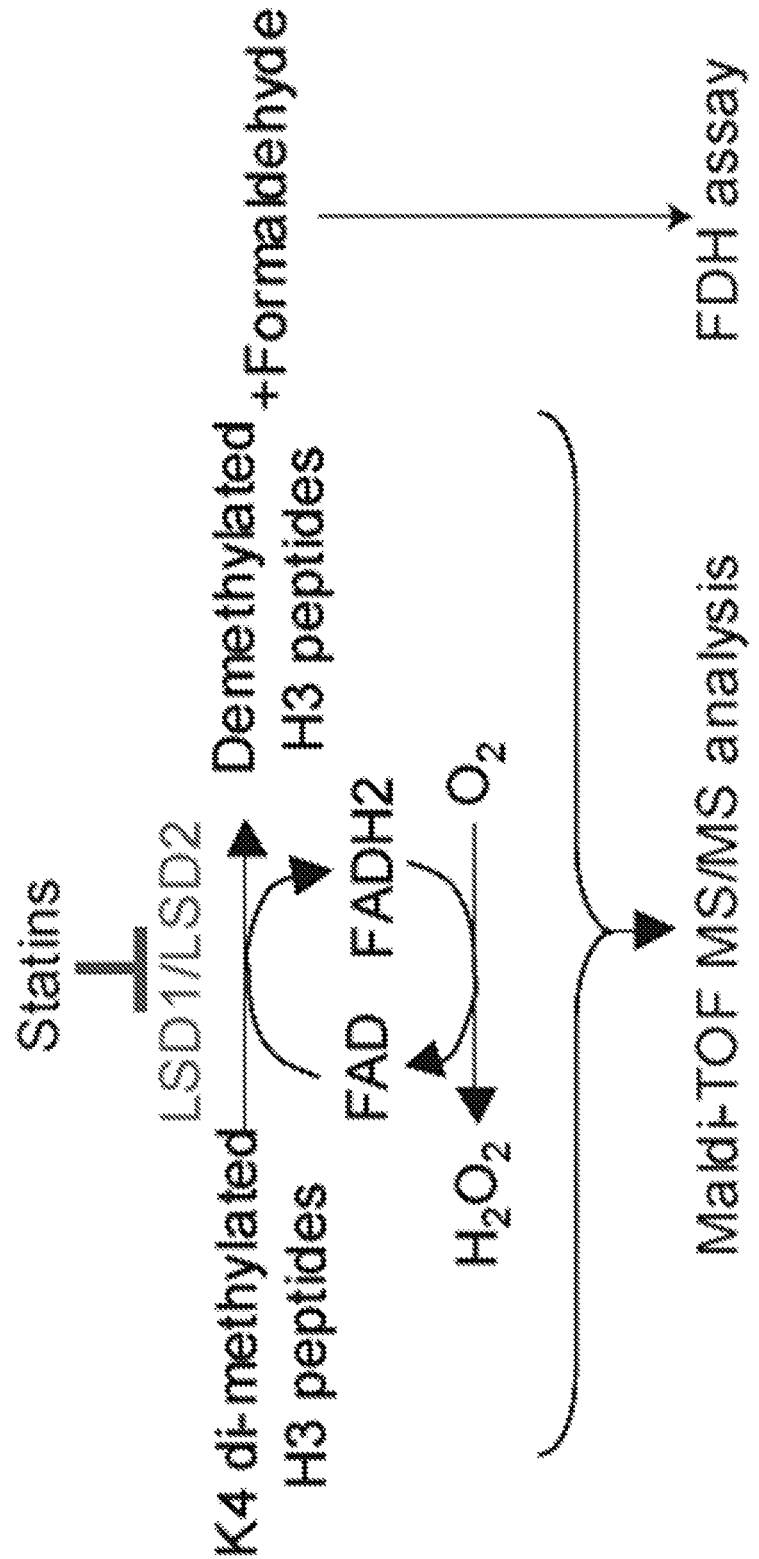
FIG. 1A shows the overview of screening for inhibitors of LSD1 histone demethylase activity. Di-methylated H3K4 peptides are incubated with purified LSD1 in the presence of statins. Demethylation of H3K4 peptides is detected by MALDI-TOF mass spectrometry and a formaldehyde dehydrogenase (FDH) assay.
Figure 1B:
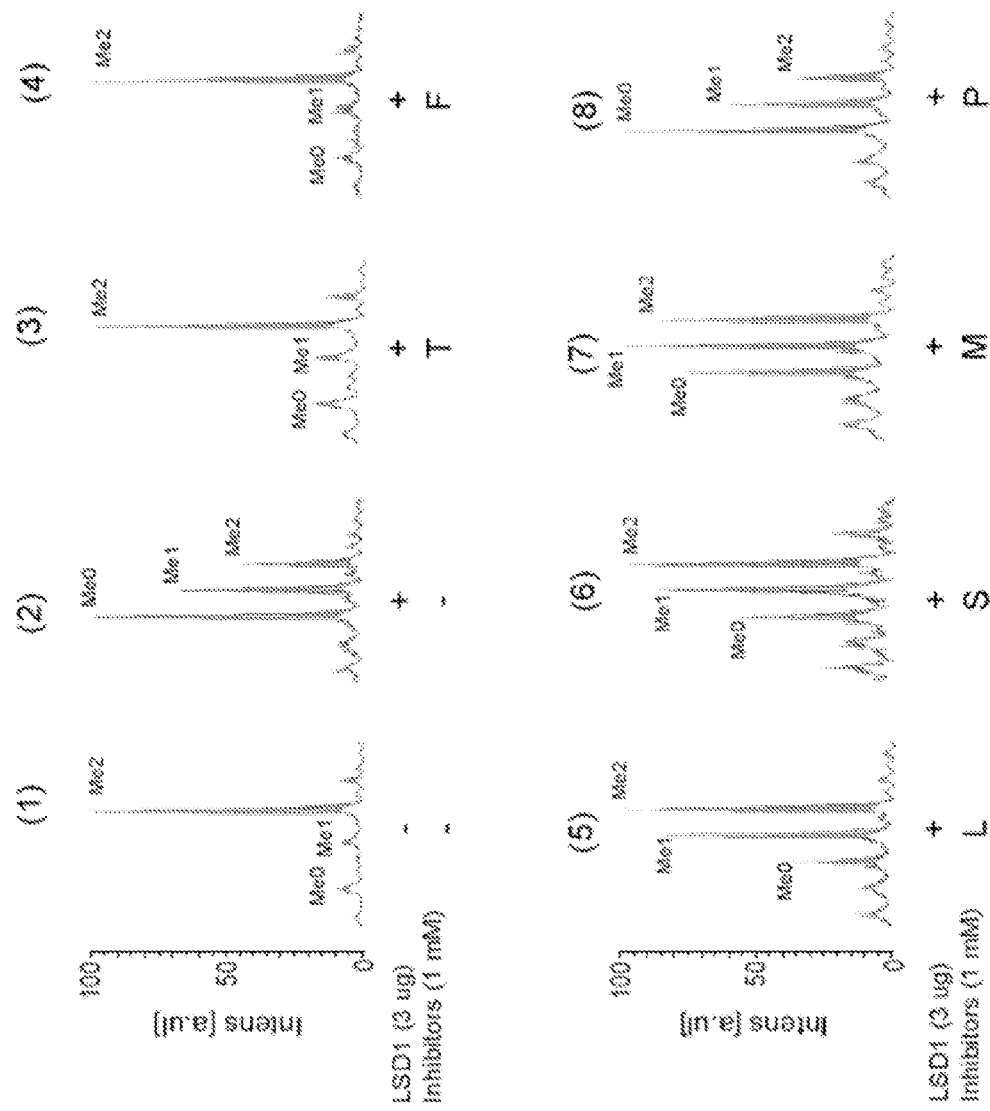
FIG. 1B shows the statins inhibit LSD1 demethylase activity on H3K4Me2. Mass spectrometry analysis of demethylation assays. H3K4Me2 peptides alone (panel 1) demonstrate a major peak at a molecular mass of 2863 Dalton (Da) as previously reported. Peptide was incubated with purified LSD1 (panel 2), or various statin compounds (panels 3-8). The decrease in dimethylated peptide (Me2) and appearance of mono-methylated peptide (Me1) at a molecular mass of 2849 or unmethylated peptide (Me0) at a molecular mass of 2835 is indicated. T, tranylcypromine; F, fluvastatin; L, lovastatin; S, simvastatin; M, mevastatin; P, pravastatin. Note: effectiveness of LSD1 inhibition is F>L>S>M>P.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the various embodiments of the disclosure was performed using standard procedures known to one skilled in the art, for example, in Maniatis et al., Molecular Cloning: A Laboratory Manual, Cold Spring Harbor Laboratory Press, Cold Spring Harbor, N.Y., USA (1982);

Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, which are all herein incorporated by reference in their entireties.

It should be understood that various embodiments of the disclosure are not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the disclosure are based on the discovery that the common cholesterol-lowing drugs, statins, inhibit histone lysine specific demethylase 1 (LSD1) and/or and a histone lysine specific demethylase 2 (LSD2) and induces cell death in the human cancer cell such as Hela cells. The cell death, apoptosis, is not mitigated by mevalonate, the by-product of HMG-CoA reductase, the target of statins, in the mevalonate pathway or HMG-CoA reductase pathway. Moreover, several cancer cell lines have elevated expression of LSD1 and/or LSD2, e.g., neuroblastoma, hepatocellular carcinoma, metastatic carcinoma, and metastatic melanoma (see FIG. 9). Accordingly, inhibiting the activity of LSD1 and/or LSD2 can be used to induce apoptosis when desired, for example, in cancer and tumor treatment. Moreover, epigenetically altering the regulation of expression of genes in chromosomes can affect the outcome of cancer and tumor treatment in a subject, for example, enhance the cancer drug efficacy, promote chemo-protection and reduce the development of chemo-resistance cancer cells.

Accordingly, in one embodiment, the disclosure herein provides a method for treating cancer in a subject comprising administering to a subject in need thereof a therapeutically effective amount of an epigenetic modulating adjuvant agent in conjunction with at least one chemotherapy, wherein the epigenetic modulating adjuvant agent promotes chemo-protection and reducing chemo-resistance. In one embodiment, the epigenetic modulating adjuvant agent enhance the drug efficacy of the at least one chemotherapy to promotes chemo-protection and reducing the development of chemo-resistance cancer cells in the subject.

In one embodiment, the disclosure herein provides a method for enhancing the drug efficacy of at least one cancer chemotherapy in a subject to promote chemo-protection and reducing the development of chemo-resistance cancer cells in the subject comprising administering to the subject in need thereof a therapeutically effective amount of at least one an epigenetic modulating adjuvant agent in conjunction with the at least one chemotherapy.

In one embodiment, the disclosure herein provides a method for treating chemotherapy resistant cancer in a subject, the method comprising determining whether chemotherapy resistant cancer cell population of the subject are susceptible to an epigenetic modulating agent; and, if so, administering to the subject a therapeutically effective amount of the epigenetic modulating agents, wherein the agent treats chemotherapy resistant cancer in the subject by inducing apoptosis of the chemotherapy resistant cancer cells, and wherein the apoptosis induced is at least 10% compared to cancer cells of the subject in the absence of the epigenetic modulating agent.

In one embodiment, the epigenetic modulating adjuvant agent is an inhibitor of a histone demethylase, (e.g., histone lysine specific demethylase 1 (LSD1) and/or and a histone lysine specific demethylase 2 (LSD2). In one embodiment, the at least one chemotherapy is an alkylating chemotherapeutic drug. In one embodiment, the alkylating chemotherapeutic drug is an alkylating antineoplastic agent. In one embodiment, the alkylating antineoplastic agent attaches an alkyl group ($C_nH_{2n+1}$) to DNA. In one embodiment, the alkylating antineoplastic agent is selected from the group consisting of cyclophosphamide, uramustine, melphalan, chlorambucil, ifosfamide, carmnnustine, lomustine, streptozocin, busulfan, cisplatin, carboplatin, nedaplatin, oxaliplatin, satraplatin, triplatin tetranitrate, procarbazine, altretamine, dacarbazine, mitozolomide, temozolomide, and temozolomide.

In one embodiment, the epigenetic modulating adjuvant agent enhance the drug efficacy of the at least one chemotherapy to promotes chemo-protection and reducing the development of chemo-resistance cancer cells in the subject. In one embodiment, the enhancement of the chemo drug efficacy is at least 5% over a control level. In other embodiments, the enhancement of the chemo drug efficacy is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least 100% over a control level.

In one embodiment, the control level is the drug efficacy of the chemotherapy drug in the absence of the epigenetic modulating adjuvant agent being administered to the subject.

In one embodiment, cancer cells can be treated with various statins to determine in vitro or ex vivo the cytotoxic/apoptotic efficacy of the tested statin. In one embodiment, the cytotoxic/apoptotic efficacy of the tested statin can be assessed by specifically testing the "histone code" alterations and/or expression level changes on the LSD1 or LSD2 target genes.

Cancer cells can be obtained from a subject diagnosed with or suspected of having cancer. For example, cancer cells can be obtained from a tissue biopsy or an excised tumor during a routine surgery to remove cancerous tumors.

Cancer cells are maintained in Dulbecco's modified Eagle's medium with 10% fetal calf serum. At the time of treatment, cells are twice with PBS and incubated with vehicle, fluvastatin, lovastatin, simvastatin or pravastatin at the dose ranges from 2 to 10 µM. The cells are harvested for RNA and CHIP analyses after 24-hour or 72-hour incubation. Cancer cells are incubated with various concentrations of statins for 1 week for soft agar assays. Cells ($5\times10^4$) are suspended in 3 ml of medium (DMEM supplemented with 2 g/ml insulin and 10% fetal calf serum) containing 0.3% agar. The mixture is added over a layer of 0.5% agar in DMEM on a 60-mm plate. Three weeks later, plates are stained with the vital stain 2-(p-isodophenyl)-3-(p-nitrophenyl)-5-phenyltertazolium chloride hydrate for 2 days. Colonies larger than 0.15 mm in diameter are scored. For cell proliferation assays, cells are performed using Cell Counting Kit-8 (Dojindo Molecular Technologies) following the manufacturer's protocol.

For gene analysis, Chromatin Immunoprecipitation (ChIP) Analysis and Quantitative Real-time RT-PCR assays can be used. Briefly, ChIP assays were carried out using EZ ChIP Kit (Upstate, 17-371) according to manufacturer's instructions with modifications. Briefly, after treatment with 1% formaldehyde, cells were harvested and sonicated in the ChIP lysis buffer to produce soluble chromatin with average sizes between 300-1000 bp. The chromatin samples were pre-cleaned for 1 hour using salmon sperm DNA/protein-G agarose beads (Upstate). Rabbit anti-LSD1 (Upstate, 07-705), anti-H3K4Me2 (Upstate, 07-030), or control antibodies (Santa Cruz, sc2027) were used for each ChIP. The antibody-chromatin complexes were immunoprecipitated with salmon sperm DNA pre-absorbed protein-G agarose beads. After extensive washing, bound chromatin was eluted, de-crosslinked, and purified using QIAquick PCR Purification Kit (Qiagen). Relative abundance of targets of interest was quantified by real-time PCR. ChIP primer sequences are as follows: SCN2A-2F, 5'-cgtgtttcaaggctacagca-3' (SEQ ID NO: 1); SCN2A-2R, 5'-ctctagcctcccaaccttcc-3' (SEQ ID NO: 2); SYN1-RE-F, 5'-tgggtfttaggaccaggatg-3' (SEQ ID NO: 3); SYN1-RE-R, 5'-ggtgctgaagctggcagt-3' (SEQ ID NO: 4). For Quantitative Real-time RT-PCR, total mRNA was extracted from 2×106 cultured Hela cells using the RNeasy Mini Kit (Qiagen Sciences, Germantown, Md.). After DNase treatment, cDNA was synthesized from RNA with the First Strand cDNA Synthesis kit (Amersham, Buckinghamshire, UK). PCR amplification reactions were performed with Cyber-Green reagent (Qiagen Sciences) for SYN1 and SCN2A. Primers used in RT-PCR were as follows: SYN1 forward (5'-cgtgcgtgtccagaagattg-3' (SEQ ID NO: 5)), reverse (5'-tgtgatcccttccgtccttg-3' (SEQ ID NO: 6)); SCN2A forward (5'-gatgaggatgatgaaaatggc-3' (SEQ ID NO: 7)), reverse (5'-ctaattttctaatagggttgaaggg-3' (SEQ ID NO: 8)). Gene expression of IL-6 and β-actin was detected by Taqman Gene Expression Assays (Applied Biosystems) using the ABI Prism 7000 Sequence Detection System. The primers for IL-6 and were purchased from Applied Biosystems. ΔΔCT method was used to determine mRNA levels. Target gene expression was normalized to β-actin levels.

In one embodiment, the disclosure herein provides a method for assessing the susceptible of a cancer cell population to at least one epigenetic modulating adjuvant agent comprising providing a population of cancer cells derived from a subject, contacting the cells with at least one epigenetic modulating adjuvant agent, and measuring the methylation on H3K4Me2-containing DNA sequences, wherein an increase in methylation on H3K4Me2-containing DNA sequences indicate that the cancer cell population is susceptible to the at least one epigenetic modulating adjuvant agent. In one embodiment, the increase is at least 10% over a control level which is methylation on H3K4Me2-containing DNA sequences in cells not treated with the at least one epigenetic modulating adjuvant agent.

In one embodiment, as used herein, the term "susceptible to the at least one epigenetic modulating adjuvant agent" with respect to cancer cell population means that the at least one epigenetic modulating adjuvant agent effects epigenetic changes to the genome of the cancer cell as measured by an increase in methylation on H3K4Me2-containing DNA sequences in the genome of the cancer cells. In another embodiment, the term "susceptible to the at least one epigenetic modulating adjuvant agent" means that the at least one epigenetic modulating adjuvant agent effects epigenetic changes to the genome of the cancer cell as measured by an increase in increased apoptosis in the population of cancer cells.

In one embodiment, the at least one epigenetic modulating adjuvant agent is a statin. In one embodiment, the at least one epigenetic modulating adjuvant agent is an inhibitor of LSD1 and/or LSD2.

In one embodiment, the cancer cells from a subject are chemotherapy resistant cancer cells.

In one embodiment, the disclosure herein provides a kit for assessing the susceptible of a cancer cell population to at least one epigenetic modulating adjuvant agent comprising at least one epigenetic modulating adjuvant agent, at least one anti-LSD1 antibody, and at least one anti-H3K4Me2 antibody. In one embodiment, the kit further comprises PCR primers comprising SCN2A-2F, 5'-cgtgtttcaaggctacagca-3' (SEQ. ID. NO: 1); SCN2A-2R, 5'-ctctagcctcccaaccttcc-3' (SEQ. ID. NO: 2); SYN1-RE-F, 5'-tgggtttaggaccaggatg-3' (SEQ. ID. NO: 3); SYN1-RE-R, 5'-ggtgctgaagctggcagt-3' (SEQ. ID. NO: 4).

In one embodiment, the disclosure herein provides a method for treating cancer in a subject comprising administering to a subject in need thereof a therapeutically effective amount of an inhibitor of a histone lysine specific demethylase 1 (LSD1) and/or and a histone lysine specific demethylase 2 (LSD2).

In one embodiment, the disclosure herein provides a method for treating cancer in a subject comprising administering to a subject in need thereof a composition comprising an inhibitor of LSD1 and/or and a LSD2.

In one embodiment, the disclosure herein provides a method for treating cancer in a subject comprising administering to a subject in need thereof a therapeutically effective amount of a statin.

In another embodiment, the disclosure herein provides a method for treating cancer in a subject comprising administering to a subject in need thereof a composition comprising at least one statin.

In another embodiment, the disclosure herein provides a method for treating cancer in a subject, the method comprising administering to the subject a therapeutically effective amount of an inhibitor of LSD1 and/or LSD2, wherein cancer cells of the subject has been determined to be susceptible to apoptosis induced by the inhibitor of LSD1 and/or LSD2.

In another embodiment, the disclosure herein provides a method for treating cancer in a subject, the method comprising administering to the subject a composition comprising an inhibitor of LSD1 and/or LSD2, wherein cancer cells of the subject has been determined to be susceptible to apoptosis induced by the inhibitor of LSD1 and/or LSD2.

In one embodiment, the disclosure herein provides a method for treating cancer in a subject comprising administering to a subject in need thereof a therapeutically effective amount of a statin, wherein cancer cells of the subject has been determined to be susceptible to apoptosis induced by the statin.

In another embodiment, the disclosure herein provides a method for treating cancer in a subject comprising administering to a subject in need thereof a composition comprising at least one statin, wherein cancer cells of the subject has been determined to be susceptible to apoptosis induced by the at least one statin in the composition.

In another embodiment, the disclosure herein provides a method for treating cancer in a subject, the method comprising first determining whether cancer cells of the subject are susceptible to apoptosis induced by an inhibitor of LSD1 and/or LSD2; and, if so, administering to the subject a therapeutically effective amount of the inhibitor of LSD1 and/or LSD2, wherein the inhibitor treats cancer in the subject.

In another embodiment, the disclosure herein provides a method for treating cancer in a subject, the method comprising first determining whether cancer cells of the subject are susceptible to apoptosis induced by an inhibitor of LSD1 and/or LSD2; and, if so, administering to the subject a composition comprising the inhibitor of LSD1 and/or LSD2, wherein the inhibitor treats cancer in the subject.

In another embodiment, the disclosure herein provides a method for treating cancer in a subject, the method comprising first determining whether cancer cells of the subject are susceptible to apoptosis induced by a statin; and, if so, administering to the subject a therapeutically effective amount of the statin, wherein the statin treats cancer in the subject.

In another embodiment, the disclosure herein provides a method for treating cancer in a subject, the method comprising first determining whether cancer cells of the subject are susceptible to apoptosis induced by at least one statin; and, if so, administering to the subject a composition comprising the at least one statin, wherein the statin treats cancer in the subject.

In one embodiment of any method described herein, the inhibitor of LSD1 and/or LSD2, or statin induces apoptosis in the cancer cells of the subject.

Statins, or 3-hydroxy-3-methylglutaryl coenzyme A (HMG-CoA) reductase inhibitors, are the most commonly used drugs for the treatment of hyperlipidemia and have well-established roles in reducing the risk of cardiovascular diseases [1-8]. A growing body of evidence suggests emerging therapeutic roles for statins in cancer [9-13], [14]. It is clear that statins have pleiotropic activities that may influence a number of cellular processes. For example, studies have indicated that by limiting the biosynthesis of mevalonate, statins can inhibit the production of downstream lipid isoprenoid intermediates, such as farnesyl PPi and geranylgeranyl PPi, important substrate precursors of post-translational prenylation for a number of proteins, including Ras, Rho, and Rac small G proteins [15], [16], [17]. As a result, the inhibition of prenylation of these proteins may affect G protein-mediated signaling pathways, which likely in turn regulate inflammatory responsiveness [10]. However, the underlying mechanism(s) for the pleiotropic effects of statins is still largely elusive. This is in part due to difficulties in ascribing all cellular effects to statin-mediated inhibition of HMG-CoA reductase and the reduction of downstream isoprenoid intermediates. Some hypotheses regarding the anti-tumor effect of statins have been raised, including that tumor cells may have lipid abnormalities and pro-inflammatory phenotypes [18], [19], [20], [21]. Thus, identifying novel cellular targets ("off-targets") of statins is critical in further understanding their role in cancer biology and broadening their future clinical applications.

At the same time, there are conflicting data suggesting that statins increased one's risk of developing cancer. Studies have found that use of any statin drug, in any amount, was associated with a significantly increased risk for prostate cancer. In addition, there was an increasing risk that came along with an increasing cumulative dose.

The dynamics of chromatin structure and the modifications of histones, which are coordinated by protein complexes containing multiple enzymatic activities, are fundamental epigenetic events underlying eukaryotic gene regulation. Among the post-translational modifications, methylation of histone proteins was long been considered to be an irreversible modification until recently in 2004 lysine-specific demethylase 1 (LSD1), the first and founding member of histone lysine demethylase family were discovered [22].

The first was histone lysine specific demethylase 1 (LSD1/KDM1) which is an flavin-dependent monoamine oxidase which can demethylate mono- and di-methylated lysines, specifically histone 3, lysines 4 and 9 (H3K4 and H3K9). This enzyme cannot demethylate tri-methylated lysines and for a short while it was thought that tri-methylated lysines may indeed be permanent modifications.

In late 2005 the Jumonji domain-containing (JmjC) histone demethylases were discovered which are able to demethylate mono-, di-, or tri-methylated lysines thereby disproving the theory that histone methylation is permanent once and for all. Although this conclusion has since come into question. Two specific JmjC histone demethylases are PHF8 and JHDM1D.

Currently, nearly 30 human lysine demethylases have been identified, and the number is growing. The lysine-specific demethylases (LSDs), LSD1 and LSD2, are homologous to monoamine oxidases and demethylate mono- and dimethyl-lysine residues, respectively [23], [24]. Consistent with the known dual functionality of LSD1 on both gene repression and activation, recent studies have shown that LSD1 plays crucial and versatile roles in controlling chromatin organization, gene regulation, hormone signaling, stem cell differentiation, and embryonic development [25-38]. Recent data have shown that LSD1 plays an important role in carcinogenesis. For example, tumor suppressor genes p53 and Rb are regulated by LSD1 ([39]; [40]; LSD1 is required for maintenance of global DNA methylation by regulating DNA methyltransferase DNMT1 ([41]; and overexpression of LSD1 is observed in various types of cancers, including neuroblastoma, prostate, breast and bladder cancers in which they repress transcription of repair pathways [39] and [42]. Additionally, LSD2 is a candidate cancer-related gene located at chromosome 6p22, a genomic region with a high incidence of chromosomal translocations, deletions, or amplifications in multiple cancer types [43]; [44]. Thus, LSD1/2 are important new targets for the development of specific inhibitors as a new class of anti-tumor drugs.

To date, few existing compounds have been shown to act as LSD1/2 inhibitors. LSD1-catalyzed histone demethylation occurs through a FAD coenzyme-mediated two-step electron transfer oxidation mechanism [22, 30]. This mechanism is very similar to that involved in amine oxidation by mono or polyamine oxidases [45-47]. Recently, classical monoamine oxidase inhibitors, (MAOI) pygrine (phenelzine) and tranylcypromine, were reported to inhibit LSD1 activity [26, 28, 48-49]. Two recent studies demonstrated that pharmacological inhibition of LSD1 and LSD2 combined with HDAC inhibitors induces apoptotic tumor cell death synergistically in glioblastoma [50] and breast cancer [51]. Thereafter, a few compounds such as tranylcypromine derivatives and analogues have been synthesized and evaluated as inhibitors of LSD1 [52]; [53] urea) and LSD2 [54].

The analysis of whether cancer cells from a subject are susceptible to apoptosis induced by an inhibitor of LSD1 and/or LSD2, or a statin can be performed by any method known in the art or as described in the Example Section. For example, a tissue sample is taken from the subject and the tissue sample is contacted with an inhibitor of LSD1 and/or LSD2, or a statin for a period of time, after which an apoptosis assay is performed. In one embodiment, the tissue sample is a tumor sample. In another embodiment, the tissue sample contains cancerous cells. In another embodiment, the tissue sample contains leukemia cells.

As used herein, a "tissue sample" refers to a portion, piece, part, segment, or fraction of a tissue which is obtained or removed from an intact tissue of a subject, preferably a human subject. In one embodiment, the tissue sample is a blood sample. In another embodiment, the tissue sample is a bone marrow sample. In one embodiment, the tissue sample is a cerebrospinal fluid sample.

As used herein, a "tumor sample" refers to a portion, piece, part, segment, or fraction of a tumor, for example, a tumor which is obtained or removed from a subject (e.g., removed or extracted from a tissue of a subject), preferably a human subject.

In one embodiment, the tissue sample is obtained from a biopsy procedure in the subject. In another embodiment, the tissue sample is obtained from a surgical procedure to remove a tumor mass from the subject.

In one embodiment of any method described herein, the method of determining whether cancer cells from a subject are susceptible to apoptosis comprises contacting a tissue sample comprising cancer cells obtained from the subject with an inhibitor of LSD1 and/or LSD2, or a statin described herein for a period of time and subsequently analyzing the apoptotic level of the cells of the contacted tissue, wherein if the apoptotic level is at least 10% above a control level, i.e., in the absence of the inhibitor of LSD1 and/or LSD2, or statin, the cancer cells are deemed susceptible to the inhibitor of LSD1 and/or LSD2, or statin tested.

In one embodiment, the method of determining whether cancer cells from a subject are susceptible to apoptosis further comprises providing a tissue sample comprising cancer cells obtained from the subject. A skilled physician or surgeon will be able to obtain a tissue biopsy or excised a tumor from a subject.

In one embodiment, the contacting period is at least one hour. In one embodiment, the contact period is at least one hour to 24 hours. In other embodiments, the contact period is at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, at least 23, or at least 24 hours. In one embodiment, the contact period is between one hour and 24 hours. In other embodiments, the contact period is two, three, four, five, six, seven, eight, nine, 10, 11, 12, 13, 14, 15, 16, 17, 18, 19, 20, 21, 22, 23, or 24 hours, including all the time periods between one to 24 hours to the minute. In other embodiments, the contacting period is between 24-72 hrs, including all the time periods between 24-72 hours to the half hour.

In one embodiment, the control level is the apoptotic level measured in the cancer cells derived from the same tissue sample of the subject and these cells have not been contacted with an inhibitor of LSD1 and/or LSD2, or a statin for the same period of contact exposure time as the experimented cancer cells. In other words, all conditions are kept identical to the experimented cancer cells except the control cancer cells are not contacted with an inhibitor of LSD1 and/or LSD2, or a statin. In one embodiment, in place of the inhibitor of LSD1 and/or LSD2, or the statin, the carrier medium of the inhibitor of LSD1 and/or LSD2, or statin is used instead.

In some embodiments, by "all conditions are kept identical to the experimented cancer cells" means that the control cancer cells are obtained from the same tissue sample as the experimented cancer cells and at the same time, the control cancer cells are cultured in the same environment and media as the experimented cancer cells, the control cancer cells are "mock" treated with the same carrier medium of the inhibitor of LSD1 and/or LSD2, or statin but the inhibitor of LSD1 and/or LSD2, or statin is not included, the control cancer cells are incubated for the same period of contact/exposure time, and are then analyzed by the same apoptosis assay as the experimented cancer cells. In one embodiment, by "all conditions are kept identical to the experimented cancer cells" means that the control cancer cells and the experimented cancer cells are tested simultaneously. In another embodiment, by "all conditions are kept identical to the experimented cancer cells" means that the control cancer cells and the experimented cancer cells are tested at a different time point after the tissue sample has been excised from the subject.

As used herein, "experimented cancer cells" refer to the cancer cells that are contacted with the inhibitor of LSD1 and/or LSD2, or statin. The inhibitor of LSD1 and/or LSD2, or statin is applied to the cancer cells in at least one carrier or medium.

As used herein, "control cancer cells" refer to the cancer cells that are contacted with the at least one carrier or medium used for contacting the inhibitor of LSD1 and/or LSD2, or statin with the experimented cancer cells but the inhibitor is not included. In other words, the "control cancer cells" is contacted with the carrier or medium but is not contacted with the inhibitor of LSD1 and/or LSD2, or statin of the experimented cancer cells. In other words, the "control cancer cells" are "mock" contacted with the same at least one carrier or medium only.

In one embodiment of any method described herein, apoptosis induced in the tested or experimented cancer cells from the subject is at least 10% compared to the control cancer cells of the subject in the absence of the inhibitor of LSD1 and/or LSD2, or statin. In some embodiments, the apoptosis induced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least 100%, including all the integer percent between 10% to 100%.

In one embodiment of any method described herein, apoptosis is measured by any method known in the art or as described herein in the Example Section. In another embodiment of any method described herein, the apoptosis is measured by a method selected from the group consisting of cell free apoptotic assay, DNA fragmentation assay, DNA laddering assay, annexin V staining and terminal transferase dUTP nick end labeling (TUNEL) assay. In some embodiments, apoptosis is analysed by any commercially available apoptosis assay kits, e.g., the Multi-Parameter Apoptosis Assay Kit by Cayman Chemical, catalog #600330 and the cytochrome C releasing Apoptosis Assay Kit by ABCAM® catalog #ab65311.

In one embodiment of any method described herein, the inhibitor of LSD1 and/or LSD2 is a statin. In another embodiment of any method described herein, the inhibitor of LSD1 and/or LSD2 is a not a statin.

In one embodiment of any method described herein, the statin is selected from the group consisting of fluvastatin, lovastatin, simvastatin, mevastatin, pravastatin, atorvastatin, and rosuvastatin. In one embodiment of any method described herein, the statin is fluvastatin.

In one embodiment of any method described herein, a combination of more than one statin is administered or included in the composition administered for cancer therapy. For example, fluvastatin and atorvastatin, fluvastatin and lovastatin, fluvastatin and simvastatin, fluvastatin and mevastatin, fluvastatin and pravastatin, or fluvastatin and rosuvastatin.

In one embodiment of any method described herein, the inhibitor of LSD1 and/or LSD2 is a monoamine oxidase inhibitor. Monoamine oxidase inhibitors (MAOIs) are a class of medications prescribed for the treatment of depression.

In one embodiment of any method described herein, the monoamine oxidase inhibitor is tranylcypromine, derivatives or analogues thereof.

Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include radioactively labeled inhibitor of LSD1 and/or LSD2, conjugates of inhibitor of LSD1 and/or LSD2 (e.g., biotin or avidin, with enzymes such as horseradish peroxidase and the like, with bioluminescent agents, chemoluminescent agents or fluorescent agents). Additionally, moieties may be added to the inhibitor of LSD1 and/or LSD2 or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of said compound or class, are also encompassed in the present invention. In one embodiment, derivatives, as used herein, also encompasses prodrugs of the inhibitor of LSD1 and/or LSD2, which are known to enhance numerous desirable qualities of pharmaceuticals (e.g., solubility, bioavailability, manufacturing, etc.).

In one embodiment of any method described herein, the inhibitor of LSD1 and/or LSD2 is selected from the group consisting of safrazine, parygline, nialamide, mebanazine, isocarboxazid, iprocozide, clorygline, cimoxatone, and beflomatone, and derivatives or analogues thereof.

In one embodiment of any method described herein, the inhibitor of LSD1 and/or LSD2 is a compound selected from the group consisting of the phenylcyclopropylamine derivatives of WO 2010143582 and the cyclopropylamine derivatives of WO 2012013727.

In one embodiment of any method described herein, the inhibitor of LSD1 and/or LSD2, or statin is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment of any method described herein, the composition comprising an inhibitor of LSD1 and/or LSD2, or statin is formulated to be administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment of any method described herein, the inhibitor of LSD1 and/or LSD2, or statin is administered in conjunction with at least one additional cancer therapy to achieve a combination cancer therapy.

In one embodiment of any method described herein, the composition comprising an inhibitor of LSD1 and/or LSD2, or statin is administered in conjunction with at least one additional cancer therapeutic to achieve a combination cancer therapy.

In one embodiment of any method described herein, the composition comprising an inhibitor of LSD1 and/or LSD2, or statin is administered in conjunction with retinoic acid.

In one embodiment of any method described herein, the composition comprising an inhibitor of LSD1 and/or LSD2 further comprises at least one additional cancer therapeutic.

In one embodiment of any method described herein, the composition comprising an inhibitor of LSD1 and/or LSD2 further comprises retinoic acid.

In one embodiment of any method described herein, wherein the at least one additional cancer therapy is selected from the group consisting of radiation therapy, chemotherapy, immunotherapy and gene therapy.

In other embodiments of any method described herein, the at least one additional cancer therapy is selected from the group consisting of growth inhibitory agents, cytotoxic agents, anti-angiogenesis agents, apoptotic agents, anti-tubulin agents, anti-HER-2 antibodies, anti-CD20 antibodies, an epidermal growth factor receptor (EGFR) antagonist, a HER1/EGFR inhibitor, a platelet derived growth factor inhibitor, a COX-2 inhibitor, an interferon, and a cytokine (e.g., G-CSF, granulocyte-colony stimulating factor).

In other embodiments of any method described herein, the at least one additional cancer therapy is selected from the group consisting of 13-cis-retinoic acid, 2-CdA, 2-Chlorodeoxyadenosine, 5-Azacitidine, azacytidine, 5-Fluorouracil, 5-FU, 6-Mercaptopurine, 6-MP, 6-TG, 6-Thioguanine, abiraterone acetate, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Cabazitaxel, Calcium Leucovorin, Campath® Camptosar® Camptothecin-11, Capecitabine, Caprelsa® Carac™ Carboplatin, Carmnnustine, Carmnnustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Crizotinib, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, Denosumab, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eculizumab, Efudex®, Eligard™, Ellence™, Eloxatin™, Elspar®, Emcyt®, Epirubicin, Epoetin Alpha, Erbitux, Eribulin, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, Gefitinib, Gemcitabine, Gemtuzumab ozogamicin, Gemzar, Gleevec™, Gliadel® Wafer, Goserelin, Granulocyte—Colony Stimulating Factor (G-CSF), Granulocyte Macrophage Colony Stimulating Factor (GM-CSF), Halaven®, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Inlyta®, Interferon alpha, Interferon Alpha-2b (PEG Conjugate), Interleukin-2, Interleukin-11, Intron A® (interferon alpha-2b), Ipilimumab, Iressa®, Irinotecan, Isotretinoin, Ixabepilone, Ixempra™, Jevtana®, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolia®, Prolifeprospan 20 with Cannustine Implant, Provenge®, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Sipuleucel-T, Soliris®, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, Valrubicin, Valstar, vandetanib, VCR, Vectibix™, Velban®, Velcade®, Vemurafenib, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xalkori capsules, Xeloda®, Xgeva®, Yervoy®, Zanosar®, Zelboraf, Zevalin™, Zinecard®, Zoladex®, Zoledronic acid, Zolinza, Zometa®, and Zytiga®.

In one embodiment of any method described herein, the method further comprises administering a drug that treats at least one symptom of cancer or cancer therapy. For example, for low blood count or anemia resulting from the chemo- or radiation therapy, erythropoietin can be administered to promote de novo the production of blood cell cells.

In one embodiment of any method described herein, wherein the subject is a mammal. In another embodiment, the subject is a primate mammal. In other embodiment, the subject is human.

In one embodiment of any method described herein, the inhibitor of LSD1 and/or LSD2, or statin or the composition further comprises a pharmaceutically acceptable carrier.

In one embodiment of any method described herein, the method further comprises selecting a subject who has cancer or has been diagnose with cancer. The subject can be screened for cancer with a combination with diagnostics such as, for example, additional biomarkers, mammography, manual examination, MRI, or tissue biopsy and histopathological examination. A skilled oncologist or physician will be able to differentially diagnosis cancer using medical diagnostic methods known within the art.

In one embodiment, the disclosure described herein provides a composition comprising at least one inhibitor of a LSD1 and/or and a LSD2, and a pharmaceutically acceptable carrier.

In one embodiment, the disclosure described herein provides a composition comprising at least one inhibitor of a LSD1 and/or and a LSD2, retinoic acid, and a pharmaceutically acceptable carrier.

In one embodiment, the disclosure described herein provides a composition comprising at least one inhibitor of a LSD1 and/or and a LSD2, at least one additional cancer therapeutic and a pharmaceutically acceptable carrier. The inhibitor of a LSD1 and/or and a LSD2 can be a statin or a non-statin molecule. For example, fluvastatin and gefitinib, fluvastatin and Taxol®, fluvastatin and crizotinib, fluvastatin and bexarotene, fluvastatin and azacitidine, fluvastatin and tamoxifen, fluvastatin and panitumumab, fluvastatin and vinorelbine tartrate, tranylcypromine and gefitinib, tranylcypromine and Taxol®, tranylcypromine and crizotinib, tranylcypromine and bexarotene, tranylcypromine and azacitidine, tranylcypromine and tamoxifen, tranylcypromine and panitumumab, tranylcypromine and vinorelbine tartrate, a phenylcyclopropylamine derivative and gefitinib, a phenylcyclopropylamine derivative and Taxol®, a phenylcyclopropylamine derivative and crizotinib, a phenylcyclopropylamine derivative and bexarotene, a phenylcyclopropylamine derivative and azacitidine, a phenylcyclopropylamine derivative and tamoxifen, a phenylcyclopropylamine derivative and panitumumab, a phenylcyclopropylamine derivative and vinorelbine tartrate, a cyclopropylamine derivative and gefitinib, a cyclopropylamine derivative and Taxol®, a cyclopropylamine derivative and crizotinib, a cyclopropylamine derivative and bexarotene, a cyclopropylamine derivative and azacitidine, a cyclopropylamine derivative and tamoxifen, a cyclopropylamine derivative and panitumumab, and a cyclopropylamine derivative and vinorelbine tartrate.

In one embodiment, the disclosure described herein provides a composition comprising at least one inhibitor of a LSD1 and/or and a LSD2, at least one additional cancer therapeutic, retinoic acid, and a pharmaceutically acceptable carrier.

In one embodiment, the disclosure described herein provides a composition comprising at least one inhibitor of a LSD1 and/or and a LSD2, at least a statin, and a pharmaceutically acceptable carrier, wherein the inhibitor of a LSD1 and/or and a LSD2 is not a statin. For example, tranylcypromine and fluvastatin, tranylcypromine and lovastatin, tranylcypromine and simvastatin, tranylcypromine and mevastatin, tranylcypromine and pravastatin, tranylcypromine and atorvastatin, and tranylcypromine and rosuvastatin.

In one embodiment, the disclosure described herein provides a composition comprising at least one inhibitor of a LSD1 and/or and a LSD2, at least a statin, retinoic acid, and a pharmaceutically acceptable carrier, wherein the inhibitor of a LSD1 and/or and a LSD2 is not a statin.

In one embodiment, the disclosure described herein provides a composition comprising at least one inhibitor of a LSD1 and/or and a LSD2, at least a statin, at least one additional cancer therapeutic and a pharmaceutically acceptable carrier, wherein the inhibitor of a LSD1 and/or and a LSD2 is not a statin. For example, tranylcypromine, gefitinib and fluvastatin; tranylcypromine, Taxol® and lovastatin; tranylcypromine, crizotinib and simvastatin; tranylcypromine, bexarotene and mevastatin; tranylcypromine, azacitidine and pravastatin; tranylcypromine, tamoxifen and atorvastatin; and tranylcypromine, panitumumab and rosuvastatin.

In one embodiment, the disclosure described herein provides a composition comprising at least one inhibitor of a LSD1 and/or and a LSD2, retinoic acid, at least a statin, at least one additional cancer therapeutic and a pharmaceutically acceptable carrier, wherein the inhibitor of a LSD1 and/or and a LSD2 is not a statin.

In one embodiment, the disclosure described herein provides a composition comprising at least one statin, at least one additional cancer therapeutic and a pharmaceutically acceptable carrier. For example, fluvastatin and gefitinib, fluvastatin and Taxol®, fluvastatin and crizotinib, fluvastatin and bexarotene, fluvastatin and azacitidine, fluvastatin and tamoxifen, fluvastatin and panitumumab, and fluvastatin and vinorelbine tartrate.

In one embodiment, the disclosure described herein provides a composition comprising at least one statin, retinoic acid, at least one additional cancer therapeutic and a pharmaceutically acceptable carrier.

In one embodiment of any composition described herein, the composition is used for the treatment of cancer.

In one embodiment, the disclosure described herein provides an inhibitor of a LSD1 and/or and a LSD2 for use in the treatment of cancer.

In one embodiment, the disclosure described herein provides an inhibitor of a LSD1 and/or and a LSD2 for use in the treatment of cancer in a subject.

In one embodiment, the disclosure described herein provides an inhibitor of a LSD1 and/or and a LSD2 and at least one additional cancer therapeutic for use in the treatment of cancer.

In one embodiment, the disclosure described herein provides an inhibitor of a LSD1 and/or and a LSD2 and a statin for use in the treatment of cancer, wherein the inhibitor of a LSD1 and/or and a LSD2 is not a statin.

In one embodiment, the disclosure described herein provides an inhibitor of a LSD1 and/or and a LSD2, a statin and at least one additional cancer therapeutic for use in the treatment of cancer, wherein the inhibitor of a LSD1 and/or and a LSD2 is not a statin.

In one embodiment, the inhibitor of LSD1 and/or LSD2 is a statin.

In one embodiment, the disclosure described herein provides a statin for use in the treatment of cancer in a subject.

In one embodiment, the statin is selected from the group consisting of fluvastatin, lovastatin, simvastatin, mevastatin, pravastatin, atorvastatin, and rosuvastatin.

In one embodiment, the statin is fluvastatin.

In one embodiment, the inhibitor of LSD1 and/or LSD2 is a monoamine oxidase inhibitor.

In one embodiment, the monoamine oxidase inhibitor is tranylcypromine, derivatives or analogues thereof.

In one embodiment, the inhibitor of LSD1 and/or LSD2, or statin is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

In one embodiment, the inhibitor of LSD1 and/or LSD2, and/or statin is administered in conjunction with at least one additional cancer therapy to achieve a combination cancer therapy.

In one embodiment of any of the composition described herein, the composition is formulated to be administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intravitreous, intratumor, and parenteral administration.

In one embodiment, of any of the composition described herein, the composition is administered in conjunction with retinoic acid.

In one embodiment, of any of the composition described herein, the composition is administered in conjunction with at least one additional cancer therapy to achieve a combination cancer therapy.

In one embodiment of any composition described herein, wherein the at least one additional cancer therapy is selected from the group consisting of radiation therapy, chemotherapy, immunotherapy and gene therapy.

In one embodiment, of any of the composition described herein, the at least one additional cancer therapy is selected from the group consisting of growth inhibitory agents, cytotoxic agents, anti-angiogenesis agents, apoptotic agents, anti-tubulin agents, anti-HER-2 antibodies, anti-CD20 antibodies, an epidermal growth factor receptor (EGFR) antagonist, a HER1/EGFR inhibitor, a platelet derived growth factor inhibitor, a COX-2 inhibitor, an interferon, and a cytokine (e.g., G-CSF, granulocyte-colony stimulating factor).

In other embodiments of any of the composition described herein, the at least one additional cancer therapy is selected from the group consisting of 13-cis-retinoic acid, 2-CdA, 2-Chlorodeoxyadenosine, 5-Azacitidine, azacytidine, 5-Fluorouracil, 5-FU, 6-Mercaptopurine, 6-MP, 6-TG, 6-Thioguanine, abiraterone acetate, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Cabazitaxel, Calcium Leucovorin, Campath® Camptosar® Camptothecin-11, Capecitabine, Caprelsa® Carac™ Carboplatin, Cannustine, Cannustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Crizotinib, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, Denosumab, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eculizumab, Efudex®, Eligard™, Ellence™, Eloxatin™, Elspar®, Emcyt®, Epirubicin, Epoetin Alpha, Erbitux, Eribulin, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, Gefitinib, Gemcitabine, Gemtuzumab ozogamicin, Gemzar, Gleevec™, Gliadel® Wafer, Goserelin, Granulocyte—Colony Stimulating Factor (G-CSF), Granulocyte Macrophage Colony Stimulating Factor (GM-CSF), Halaven®, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Inlyta®, Interferon alpha, Interferon Alpha-2b (PEG Conjugate), Interleukin-2, Interleukin-11, Intron A® (interferon alpha-2b), Ipilimumab, Iressa®, Irinotecan, Isotretinoin, Ixabepilone, Ixempra™, Jevtana®, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Oraprred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolia®, Prolifeprospan 20 with Cannustine Implant, Provenge®, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Sipuleucel-T, Soliris®, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, Valrubicin, Valstar, vandetanib, VCR, Vectibix™, Velban®, Velcade®, Vemurafenib, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xalkori capsules, Xeloda®, Xgeva®, Yervoy®, Zanosar®, Zelboraf, Zevalin™, Zinecard®, Zoladex®, Zoledronic acid, Zolinza, Zometa®, and Zytiga®.

In one embodiment of the combination cancer therapy, the inhibitor of LSD1 and/or LSD2, or statin can be administered simultaneously with the at least one additional cancer therapy or sequentially. In one embodiment, simultaneous administration can be achieve when the inhibitor of LSD1 and/or LSD2, or statin and the at least one additional cancer therapy are in one composition.

Formulation and Administration

In one embodiment, the inhibitor of LSD1 and/or LSD2, or statin is delivered in a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

As used herein, in one embodiment, "administering" refers to the placement of an inhibitor of LSD1 and/or LSD2, or statin into a subject by a method or route which results in at least partial localization of the inhibitor or statin at a desired site. The inhibitor of LSD1 and/or LSD2, or statin can be administered by any appropriate route which results in effective treatment in the subject, i.e. administration results in delivery to a desired location (e.g., directly to a tumor or near a tumor) in the subject where at least a portion of the composition delivered, i.e. at least an inhibitor or statin which inhibits LSD1 and/or LSD2 activity, is active in the desired site for a period of time. The period of time the LSD1/2 inhibitor is active depends on the half-life in vivo after administration to a subject, and can be as short as a few hours, e.g. twenty-four hours, to a few days, to as long as several years. Modes of administration include injection, infusion, instillation, suppository (e.g., for vaginal, cervical. rectal or urethral insertion), percutaneous implantation or ingestion. "Injection" includes, without limitation, intravenous, intramuscular, intraarterial, intraventricular, intradermal, intraperitoneal, subcutaneous, subcuticular injection and infusion.

Therapeutic compositions contain a physiologically tolerable carrier together with at least an inhibitor of LSD1 and/or LSD2, or statin as described herein, dissolved or dispersed therein as an active ingredient. In one embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Compositions can be prepared as injectable either as liquid solutions or suspensions, however, solid forms suitable for solution, or suspensions; in liquid prior to use can also be prepared. The preparation can also be emulsified or presented as a liposome composition. The inhibitors of LSD1 and/or LSD2, or statin can also be conjugated with lipids, e.g., amphipathic lipids, for stability and delivery purposes. The conjugation bonds are reversible and are broken or dissolved when the inhibitors of LSD1 and/or LSD2, or statin are delivered to target destination. Alternatively, the inhibitors of LSD1 and/or LSD2, or statin described herein can be prepared as a solid or semi-solid or emulsion in suppository, e.g., as microspheres. The microspheres can be inserted as a solid into or targeted to a solid tumor. The inhibitors of LSD1 and/or LSD2, or statin described herein can be mixed with excipients which are pharmaceutically acceptable and compatible with the active ingredient and in amounts suitable for use in the therapeutic methods described herein. Specifically contemplated pharmaceutical compositions are inhibitors of LSD1 and/or LSD2, or statin in a preparation for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition comprising the inhibitors of LSD1 and/or LSD2, or statin described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of inhibitors of LSD1 and/or LSD2, or statin used in the methods described herein that will be effective in the treatment of a particular disorder or condition will depend on the nature of the disorder or condition, and can be determined by standard clinical techniques.

Routes of administration include, but are not limited to, direct injection, intradermal, intramuscular, intraperitoneal, intravenous, subcutaneous, intrauterine and oral routes. The inhibitors of LSD1 and/or LSD2, or statin or compositions described herein can be administered by any convenient route, for example by infusion, intravenous injection, suppository or bolus injection, by absorption through epithelial or mucocutaneous linings (e.g., oral mucosa, rectal and intestinal mucosa, etc.) and may be administered together with other biologically active agents. Administration can be systemic or local.

The precise dose and formulation to be employed depends upon the potency of the inhibitor, and include amounts large enough to produce the desired effect, e.g., a reduction in size and/or growth of the tumors in the subject. The dosage should not be so large as to cause unacceptable adverse side effects. Generally, the dosage will vary with the type of inhibitor of LSD1 and/or LSD2, or statin, and with the age, condition, and size of the tumors in the subject are also considered. Dosage and formulation of the inhibitor of LSD1 and/or LSD2, or statin will also depend on the route of administration, and the mass and number of tumors in the subject, and should be decided according to the judgment of the practitioner and each subject's circumstances. Effective doses can be extrapolated from dose-response curves derived from in vitro or animal model test systems.

The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 g/kg body weight to 30 g/kg body weight. Alternatively, the dose range will be titrated to maintain serum levels between 5 g/mL and 30 g/mL.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy, e.g., shrinkage of tumor sizes. Continuous, relatively low maintenance doses are contemplated after an initial higher therapeutic dose. As exemplary, the inhibitor of LSD1 and/or LSD2, or statin and a pharmaceutically acceptable carrier can be formulated for direct application by injection into the tumor in the subject.

Efficacy testing can be performed during the course of treatment using the methods described herein, e.g., ultrasound, MRI and CT to monitor the shrinkage in size of the tumors in the treated subject. A decrease in size of the tumors during and after treatment indicates that the treatment is effective in reducing tumor size. Measurements of the degree of severity of a number of symptoms associated with cancerous tumors are also noted prior to the start of a treatment and then at later specific time period after the start of the treatment. A skilled physician will be able to ascertain the tumor sizes and related symptoms by known methods in the art and those described herein.

The present invention can be defined in any of the following numbered paragraphs:

[1] A method for treating cancer in a subject comprising administering to a subject in need thereof a therapeutically effective amount of an inhibitor of a histone lysine specific demethylase 1 (LSD1) and/or and a histone lysine specific demethylase 2 (LSD2).

[2] A method for treating cancer in a subject, the method comprising administering to the subject a therapeutically effective amount of the inhibitor of LSD1 and/or LSD2, wherein cancer cells of the subject has been determined to be susceptible to apoptosis induced by the inhibitor of LSD1 and/or LSD2.

[3] A method for treating cancer in a subject, the method comprising (a) determining whether cancer cells of the subject are susceptible to apoptosis induced by an inhibitor of LSD1 and/or LSD2; and, if so, (b) administering to the subject a therapeutically effective amount of the inhibitor of LSD1 and/or LSD2, wherein the inhibitor treats cancer in the subject.

[4] The method of paragraph 2 or 3, wherein the apoptosis induced is at least 10% compared to cancer cells of the subject in the absence of the inhibitor of LSD1 and/or LSD2.

[5] The method of any one of paragraphs 2-4, wherein the apoptosis is measured by a method selected from the group consisting of a cell free apoptotic assay, a DNA fragmentation assay, a DNA laddering assay, an Annexin V staining assay, and a terminal transferase dUTP nick end Labeling (TUNEL) assay.

[6] The method of any one of paragraphs 1-5, wherein the inhibitor of LSD1 and/or LSD2 is a statin.

[7] The method of paragraph 6, wherein the statin is selected from the group consisting of fluvastatin, lovastatin, simvastatin, mevastatin, pravastatin, atorvastatin, and rosuvastatin.

[8] The method of paragraph 7, wherein the statin is fluvastatin.

[9] The method of any one of claims 1-5, wherein the inhibitor of LSD1 and/or LSD2 is a monoamine oxidase inhibitor.

[10] The method of paragraph 9, wherein the monoamine oxidase inhibitor is tranylcypromine, derivatives or analogues thereof.

[11] The method of any of paragraphs 1-10, wherein the inhibitor of LSD1 and/or LSD2 is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

[12] The method of any one of paragraphs 1-11, wherein the inhibitor of LSD1 and/or LSD2 is administered in conjunction with at least one additional cancer therapy to achieve a combination cancer therapy.

[13] The method of any one of paragraphs 1-12, wherein the at least one additional cancer therapy is selected from the group consisting of radiation therapy, chemotherapy, immunotherapy and gene therapy.

[14] The method of any of paragraphs 1-13, wherein the subject is human.

[15] The method of any of paragraphs 1-14, wherein the inhibitor of LSD1 and/or LSD2 further comprises a pharmaceutically acceptable carrier.

[16] An inhibitor of a histone lysine specific demethylase 1 (LSD1) and/or and a histone lysine specific demethylase 2 (LSD2) for use in the treatment of cancer in a subject.

[17] The inhibitor of paragraph 16, wherein the inhibitor of LSD1 and/or LSD2 is a statin.

[18] The inhibitor of paragraph 17, wherein the statin is selected from the group consisting of fluvastatin, lovastatin, simvastatin, mevastatin and pravastatin.

[19] The inhibitor of paragraph 18, wherein the statin is fluvastatin.

[20] The inhibitor of paragraph 16, wherein the inhibitor of LSD1 and/or LSD2 is a monoamine oxidase inhibitor.

[21] The inhibitor of paragraph 20, wherein the monoamine oxidase inhibitor is tranylcypromine, derivatives or analogues thereof.

[22] The inhibitor of any one of paragraphs 16-21, wherein the inhibitor is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

[23] The inhibitor of any one of paragraphs 16-22, that is administered in conjunction with at least one additional cancer therapy to achieve a combination cancer therapy.

This invention is further illustrated by the following example which should not be construed as limiting. The contents of all references cited throughout this application, as well as the figures and cited references are incorporated herein it their entirety by reference.

Those skilled in the art will recognize, or be able to ascertain using not more than routine experimentation, many equivalents to the specific embodiments of the invention

EXAMPLES

Example 1

Statins as Histone Demethylases LSD1 and LSD2 Inhibitors and Inducers of Apoptosis in Cancer Cells Statins (HMG-CoA reductase inhibitors) are widely used for the treatment of hyperlipidemia, and have an established role in the reduction of mortality and morbidity of coronary artery diseases. Large clinical trials have demonstrated that statins have lipid-independent pleiotropic effects, including chemo-preventive effects and adjuvant chemotherapeutic effects in cancer treatment. However, the mechanism(s) of such anti-tumor activity are largely unknown. Recent data have shown histone demethylases LSD1 and LSD2 to play important roles in cancer by affecting gene regulation through chromatin remodeling. Disclosed here for the first time is the discovery that statins inhibit LSD1 and LSD2 in vitro and in vivo, providing a novel epigenetic mechanism relevant to anti-tumor activity. Inhibition of histone demethylase activity by statins in cells results in direct epigenetic profile changes of LSD1/2-associated genes, and consequent alteration of expression of LSDs target genes. These data indicate that histone demethylases are previously unrecognized cellular targets of statins, and inhibition of LSD1/2 activity may be an underlying mechanism whereby statins act on the gene expression programs. These findings provide novel insights into understanding the lipid-independent pleiotropic effects of statins and may directly link the action of statins to the epigenetic regulation of functional cancer genome.

Materials and Methods

Peptides, Histones, Antibodies, and Reagents—Synthetic histone peptides with specific modifications as well as antibodies (Ab) that recognize different histone modifications were purchased from Upstate Group, Inc (Lake Placid, N.Y.) (UP) or ABCAM Ltd (Cambridge, United Kingdom). Bulk histones were purchased from Sigma (catalogue #H9250). Formaldehyde dehydrogenase (EC1.2.1.46) purified from *Pseudomonas putida* was purchased from Sigma (F1879). All statins were purchased from Calbiochem (CA).

MALDI Mass Spectrometry (Matrix-Assisted Laser Desorption/Ionization Mass Spectroscopy)—Two microliters of the 100 µl demethylation reaction mixture was desalted by passing through a C18 ZipTip (Millipore). Prior to desalting, the ZipTips were activated and equilibrated using 10 µl of 50% acetonitrile/0.1% TFA (2×), followed by 10 µl of 0.1% trifluoroacetic acid (TFA) (3×). The reaction mixture was then loaded onto the activated ZipTips. The ZipTips were washed with 10 µl of 0.1% TFA (5×), and the bound material was eluted from the ZipTip using 2 µl of 70% acetonitrile containing 1 mg/ml α-cyano-4-hydroxycinnamic acid MALDI matrix and 0.1% TFA. The eluates were spotted onto a circle of open MALDI target areas to allow solvent evaporation and peptide/matrix cocrystallization. The samples were analyzed by a MALDI-TOF/TOF mass spectrometer (Ultraflex, Bruker Daltonics, Billerica, Mass.) at the PFPC core facility of Department of Pathology, Harvard Medical School.

Demethylase Assay—For a typical reaction, the volume of the reaction is 100 µl, in which either 6 µg bulk histone, or 3 ug nucleosome, or 3 µg of modified histone peptides were used as substrates. Substrate were incubated with 3 g purified recombinant LSD1 in the histone demethylase assay buffer 1 (50 mM Tris pH 8.5, 50 mM KCl, 5 mM $MgCl_2$, 0.5% BSA, and 5% glycerol) from 30 min up to 4 hr at 37° C. Inhibitors were first pre-incubated with enzyme in reaction buffer without substrate for 20 mins, and then substrates were added to initiate the reaction. The demethylation of histone and nucleosome substrates was analyzed by SDS-PAGE/Western blotting using methylation-specific antibodies. The demethylation of histone peptides was analyzed either by formaldehyde dehydrogenase assay or by mass spectrometry.

Formaldehyde Dehydrogenase Assay—Formaldehyde formation of demethylation reactions was continuously monitored by a coupled spectrophotometric assay [55]. LSD1 was first incubated in buffer containing 50 mM potassium phosphate, pH 7.2, 2 mM NAD+, and 0.1 U FDH (100 µl reaction volume) at 37° C. for 5 min without substrate. The demethylation-FDH-coupled reaction was initiated by the addition of the substrates. The absorbance at 340 nm was measured at each time point in a 0.5 min interval using Beckman DU640 spectrophotometer. Over a 6 min period, a kinetic software program automatically recorded the absorbance at each time point. Standard curves were obtained using various concentrations of formaldehyde diluted from 37% formaldehyde solution (Fisher Scientific, Pittsburgh, Pa.).

Calculation of $IC_{50}$ of Fluvastatin—In the fluvastatin-inhibited endogenous LSD1 demethylase activity assay, Western blot films were scanned and desitometric analysis was performed using Image J software (NIH, Bethesda, Md.). The percentage of substrate conversion was used to represent the activity of LSD1. The $IC_{50}$ of fluvastatin was calculated using sigmoidal dose response analysis with GraphPad Prism 4 software (GraphPad Software, La Jolla, Calif.).

Cell Culture and Statin Treatment—HeLa-S stable cell lines transfected by either empty vector (MOCK) or pOZ-LSD1 expressing Flag-HA tagged LSD1 (Flag-LSD1) were maintained in Dulbecco's modified Eagle's medium with 10% fetal calf serum. At the time of treatment, cells were washed twice with PBS and incubated with vehicle, fluvastatin, lovastatin, simvastatin or pravastatin at the dose ranges from 2 to 10 µM. The cells were harvested for RNA and CHIP analyses after 24-hour or 72-hour incubation.

Chromatin Immunoprecipitation (ChIP) Analysis—ChIP assays were carried out using EZ ChIP Kit (Upstate, 17-371) according to manufacturer's instructions with modifications. Briefly, after treatment with 1% formaldehyde, cells were harvested and sonicated in the ChIP lysis buffer to produce soluble chromatin with average sizes between 300-1000 bp. The chromatin samples were pre-cleaned for 1 hour using salmon sperm DNA/protein-G agarose beads (Upstate). Rabbit anti-LSD1 (Upstate, 07-705), anti-H3K4Me2 (Upstate, 07-030), or control antibodies (Santa Cruz, sc2027) were used for each ChIP. The antibody-chromatin complexes were immunoprecipitated with salmon sperm DNA pre-absorbed protein-G agarose beads. After extensive washing, bound chromatin was eluted, de-crosslinked, and purified using QIAquick PCR Purification Kit (QIAGEN). Relative abundance of targets of interest was quantified by real-time PCR. ChIP primer sequences are as follows: SCN2A-2F, 5'-cgtgtttcaaggctacagca-3' (SEQ. ID. NO: 1); SCN2A-2R, 5'-ctctagcctcccaaccttcc-3' (SEQ. ID. NO: 2); SYN1-RE-F, 5'-tgggtttaggaccaggatg-3' (SEQ. ID. NO: 3); SYN1-RE-R, 5'-ggtgctgaagctggcagt-3' (SEQ. ID. NO: 4).

Quantitative Real-time RT-PCR-Total mRNA was extracted from $2\times10^6$ cultured Hela cells using the RNEASY Mini Kit (Qiagen Sciences, Germantown, Md.). After DNase treatment, cDNA was synthesized from RNA with the First Strand cDNA Synthesis kit (Amersham, Buckinghamshire, UK). PCR amplification reactions were performed with CyberGreen reagent (Qiagen Sciences) for SYN1 and SCN2A. Primers used in RT-PCR were as follows: SYN1 forward (5'-cgtgcgtgtccagaagattg-3') (SEQ. ID. NO: 5), reverse (5'-tgtgatcccttccgtccttg-3') (SEQ. ID. NO: 6); SCN2A forward (5'-gatgaggatgatgaaaatggc-3') (SEQ. ID. NO: 7), reverse (5'-ctaattttctaatagggttgaaggg-3') (SEQ. ID. NO: 8). Gene expression of IL-6 and β-actin was detected by Taqman Gene Expression Assays (Applied Biosystems) using the ABI Prism 7000 Sequence Detection System. The primers for IL-6 and were purchased from Applied Biosystems. ΔΔCT method was used to determine mRNA levels. Target gene expression was normalized to β-actin levels.

Computational Docking and Modeling—The analysis was performed using Schrödinger's applications Maestro, Glide and Ligprep. (Schrödinger LLC). Coordinates of human lysine specific demethylase (Yong Chen et al, PDB code 2HKO) were first truncated to remove the tower and the SWIRM domain and subsequently prepared for docking using the protein preparation wizard. During the preparation step all water molecules were removed, hydrogen atoms were added and the structure was minimized to an RMSD of 0.3 $Å^2$. The prepped coordinates together with partial charges were used to calculate a cubic grid box, which extended from the active site pocket allowing ligands up to 20 Å in length to be fitted. The full docking set consisted of five statins as well as one thousand compounds from a decoy set. The statin molecules in hydroxy-acid form were prepared and minimized in Ligprep with OPLS-2005 forcefield and subsequently combined with the 1K Drug-Like Ligand Decoys Set (Schrödinger LLC). All docking calculations were done in Glide extra precision (Glide XP), with soften potential of nonpolar ligand atoms (scaling factor of 0.8) and including ligands' partial charges.

Statistical analyses. Data are given as means±s.e.m. Statistical comparisons between two experimental groups were accomplished by two tail-unpaired t-test performed with GraphPad Prism Software. P value<0.05 is considered as significant.

Results

Figure 3:
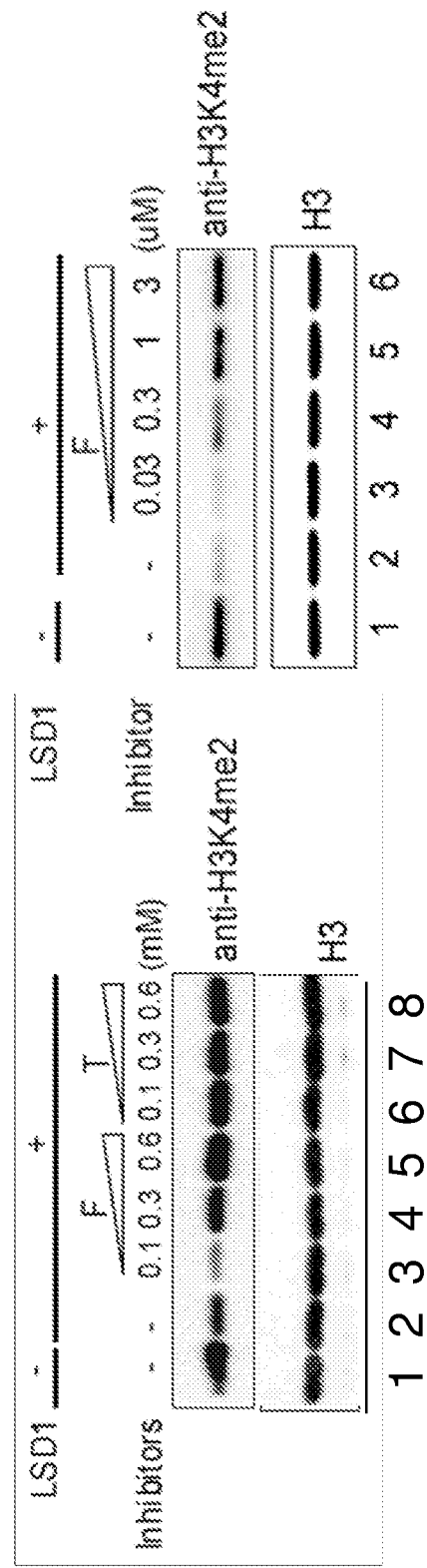
FIGS. 3A-3B show that statins inhibit LSD1 activity on histones and nucleosomes.
Figure 4:
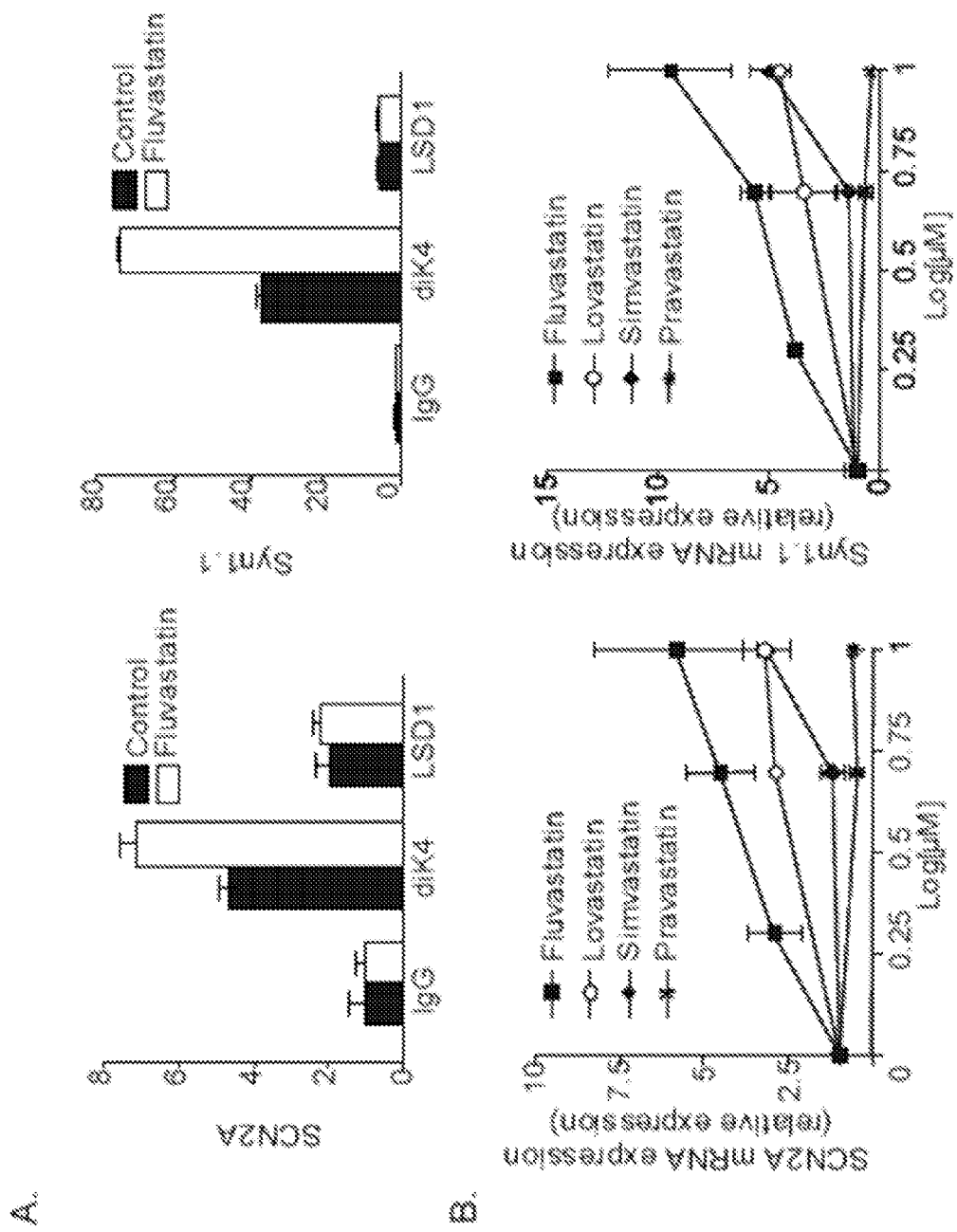
FIGS. 4A-4D show that statin regulates LSD1 target gene transcription in vivo.
Figure 4:
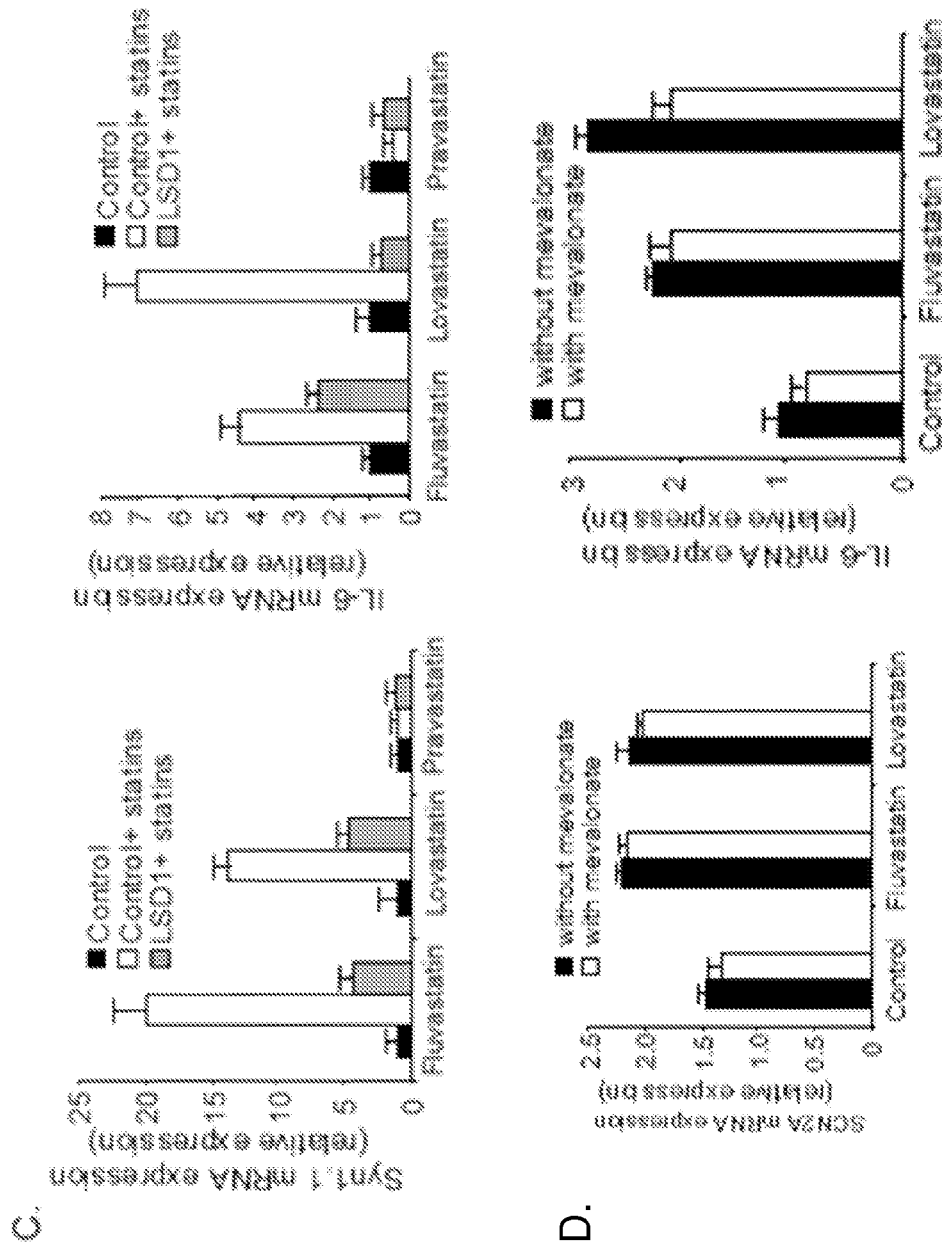

Statins inhibit the demethylase activity of LSD1 toward specific histone mark. Demethylation of a dimethyl-K4 histone H3 (H3K4Me2) by LSD1 generates unmodified histone H3 with the net loss of 28 Da, equal to the molecular weight of two $CH_2$. It was previously reported that this loss can be readily detected by mass spectrometry, using synthetic H3K4Me2 peptide as substrate [22]. Based on this MALDI-TOF mass spectrometry-based demethylase assay, an LSD1 inhibitor screening scheme was developed to test a number of statins for LSD1 inhibitor activity (FIG. 1A). Statins were first analyzed whether they could directly inhibit LSD1 H3K4Me2 demethylase activity. As expected, the mock-treated diMeK4H3 peptide (Me2) peaked at a molecular mass of 2864 Da (Me2). Incubation of the same peptide with recombinant LSD1 (rLSD1) enzyme decreased the 2864 Da peak and resulted in the generation of two new peaks, 2850 Da (Me1) and 2836 Da peaks (Me0), corresponding to the two expected demethylation products monoMeK4H3 (Me1) and unmodified histone H3 peptide (Me0), respectively. Addition of 1 mM of fluvastatin (F, FIG. 1B4), lovastatin (L, FIG. 1B5), simvastatin (S, FIG. 1B6), or mevastatin (M, FIG. 1B7) reduced the LSD1-mediated conversion of substrate diMeK4H3 to monoMeK4H3 and unmodified histone H3 (FIG. 1B4-7). Tranylcypromine (T, FIG. 1B3), a monoamine oxidase inhibitor that was recently shown to inhibit LSD1 activity, inhibited LSD1 activity under the same assay conditions (20, 37-39), thus serving as a positive control for the assay. The extent of inhibition was dependent on the specific statin tested. For example, fluvastatin completely inhibited rLSD1 activity, while the same concentration of mevastatin had less effect. Pravastatin (P, FIG. 1B8) showed no effect on the rLSD1 enzymatic activity. The effectiveness of these statins in inhibiting rLSD1 activity under these experimental conditions was in the order of F>L>S>M>P. Collectively, the results indicate that certain, but not all, statins inhibit histone demethylase LSD1 activity.

Figure 2A:
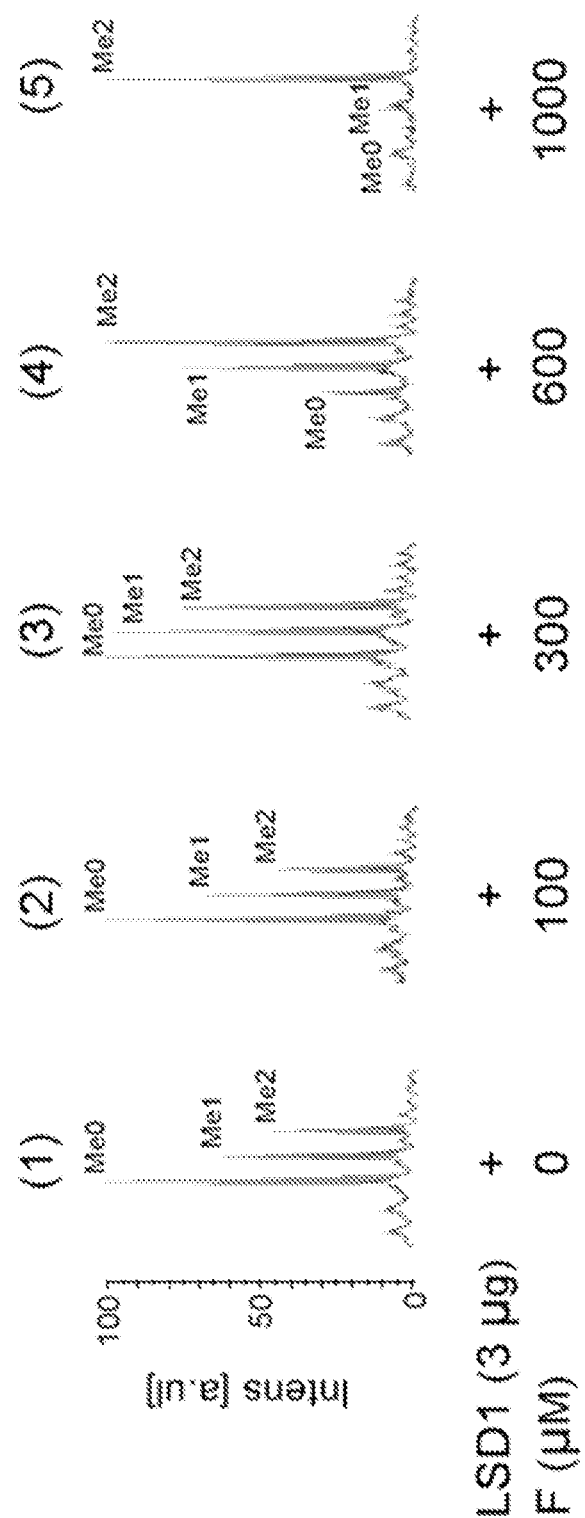
FIG. 2A shows that fluvastatin inhibits LSD1 activity in peptide demethylases assays in a dose-dependent manner. H3K4Me2 peptides were incubated with LSD1 alone (panel 1) or LSD1 plus increasing concentrations of fluvastatin (F) (panels 2-5).
Figure 2B:
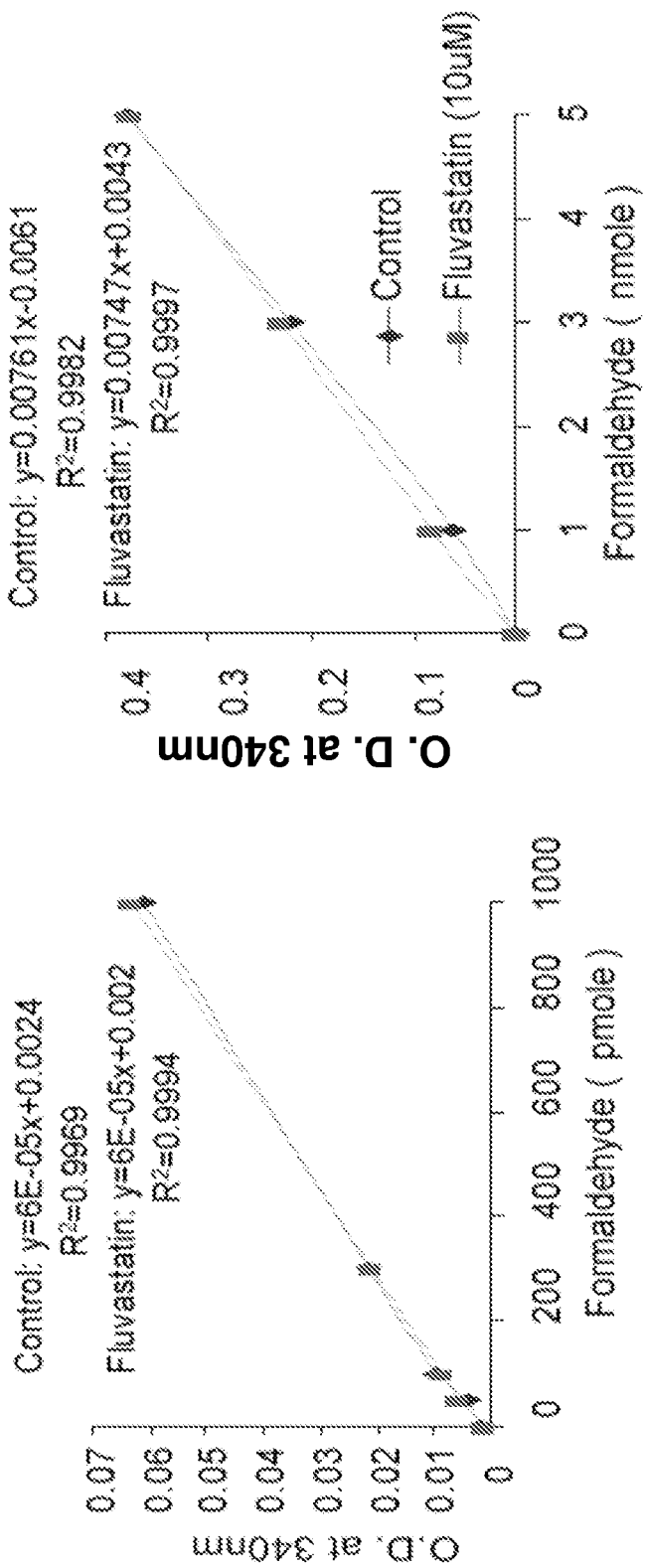
FIG. 2B shows the standard curve for formaldehyde dehydrogenase (FDH)-based assay. Formaldehyde production was monitored by measuring NADH generation at OD 340 nm. Formaldehyde was detectable in a range from 0.001 to 1 nmole (left panel) and 1 to 5 nmole (right panel); reactions were performed with 10 µM fluvastatin (square) or without (diamond). Note: fluvastatin does not affect the standard curve.

Kinetic study of the inhibition of LSD1 by fluvastatin. It was next demonstrated that the inhibition of recombinant LSD1 by statins is dose dependent using the MALDI-TOF mass spectrometry-based assay (FIG. 2A). Increasing the concentration of fluvastatin from 0 to 1000 μM resulted in a dose-dependent inhibition of LSD1 activity, as manifested by the decrease in the demethylation products H3K4Me0 and H3K4Me1 and a corresponding increase in the H3K4Me2 substrate (FIG. 2A1-4). Similar to fluvastatin, lovastatin and simvastatin also inhibited LSD1 activity, although they required higher concentrations to achieve complete inhibition (data not shown).

Figures 2C, 2D:
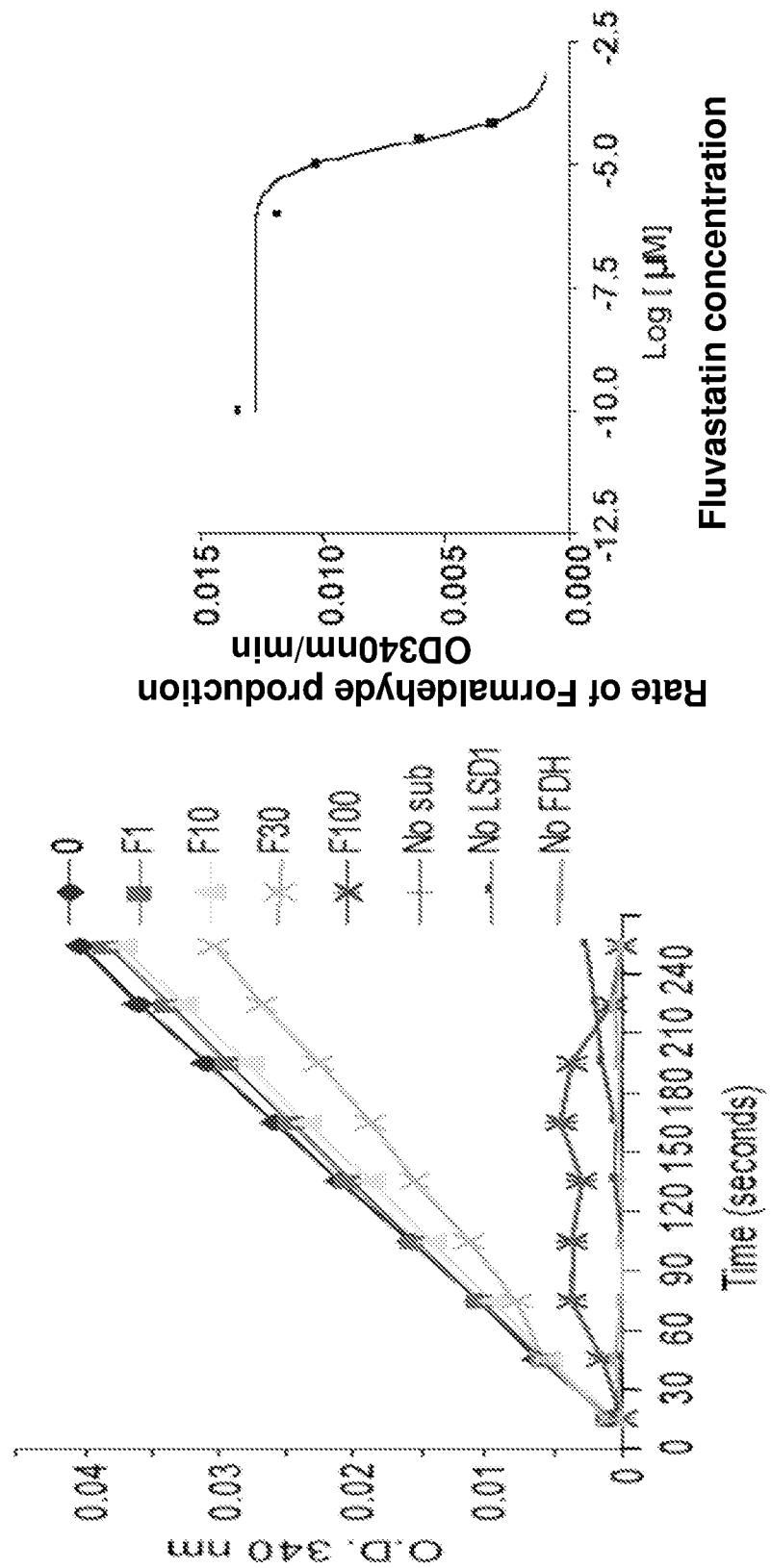
FIG. 2C shows the kinetic analysis of statin-mediated LSD1 inhibition. 10 µg of LSD1 was incubated with H3K4Me2 peptide and increasing amounts of fluvastatin. Formaldehyde production was determined every 30 seconds for 240 seconds in an optimized FDH assay. Fluvastatin concentrations: 0 µM (F0), 1 µM (F1), 10 M (F10), 30 µM (F30) and 100 µM(F100). "No sub"=reaction minus peptide; "No LSD1"=reaction minus LSD1; "No FDH"=reaction minus FDH.
FIG. 2D shows the dose response curve of LSD1 activity. LSD1 enzymatic activity is expressed as the rate of formaldehyde production, calculated as the slope (OD/min) of each linear curve generated as described in FIG. 2C, versus fluvastatin concentration, shown in log scale.

Further characterization of LSD1 inhibition by statins was performed using fluvastatin, one of the most potent LSD1 inhibitors was tested, using an optimized formaldehyde dehydrogenase FDH-coupled demethylation assay. This is a sensitive and reliable assay that measures the formaldehyde product generated from the LSD1 demethylation reaction (FIG. 1A). As demonstrated previously, the assay detects concentrations of formaldehyde ranging from 0.01 nmole up to 5 nmole in a 100 μl reaction volume by simply measuring O.D. at 340 nm to reflect the amount of NAD/NADH conversion (16). Importantly, there was a linear correlation between the formaldehyde concentration and NAD/NADH conversion in the presence of fluvastatin, indicating that these agents (FIG. 2B) do not interfere with the FDH-demethylase activity assay. As shown in FIG. 2C, in the absence of fluvastatin (F0), the addition of rLSD1 enzyme to the FDH-coupled demethylase assay reaction generates an almost linear increase of OD340 value over a period of four minutes. The linearity of the data indicate the steady state of the reaction, and thus, the slope that represents the rate of formaldehyde production can be calculated and converted to the rLSD1 activity (FIG. 2D). As the concentration of fluvastatin increased, the slopes of the corresponding reaction curves decreased (FIG. 2C), reflecting diminished rLSD1 demethylase activity. While low concentrations of fluvastatin (1-10 μM) had little effect on rLSD1 demethylase activity, a dramatic decrease in activity was seen at 30 μM with almost complete inhibition at 100 M (FIGS. 2C&D). No product was detected over the period of time monitor in this experiment where the substrate, LSD1 enzyme, or FAD was omitted. In FIG. 2D, a dose-response curve was plotted. The $EC_{50}$ of fluvastatin in this particular experiment condition is about 25 μM. Thus, with both MALDI-TOF mass spectrometry analysis and FDH coupled demethylase analysis, fluvastatin was shown to be a LSD1 inhibitor in vitro.

Statins inhibit LSD1 activity on histones and nucleosomes. To ascertain whether statins inhibit LSD1 activity on more relevant substrates, such as core histones and native substrate nucleosomes, another LSD1 demethylase assay using an antibody that specifically recognizes H3K4Me2 on bulk histones and nucleosomes was performed. Consistent with the peptide/MALDI-TOF mass spectrometry assay results, fluvastatin inhibited LSD1 demethylase activity on bulk histones in a dose dependent manner (FIG. 3A, lane 3-5).

It was next demonstrated that statins inhibit native LSD1 activity on its physiological substrate nucleosome, using the purified TAP-CtBP complex as enzyme source, which contains active endogenous LSD1 and its cofactor CoREST (27, 40-42). As shown in FIG. 3B, The CtBP complex was purified from HeLa cells and shown to efficiently demethylate H3K4Me2 on nucleosomes (lane 2) (17, 19). Fluvastatin had a dramatic inhibitory effect on the LSD1 activity when nucleosomes were used as substrate (FIG. 3B, lane 4-6). This inhibition was seen at low concentrations with an $IC_{50}$ of 0.30 M (FIG. 3B, lane 4), and was almost complete at a concentration of 3 uM (lane 6), indicating fluvastatin is even more potent towards the native enzyme. Importantly, the $IC_{50}$ of native LSD1 falls into the range of fluvastatin serum concentrations in patients taking this medication (43).

Effect of statins on the expression of LSD1-regulated target genes in vivo. Since LSD1 reduces the extent of H3K4Me2, it was reasoned that inhibition of LSD1 by statins would lead to increased levels of H3K4 dimethylation on the well-characterized LSD1 target gene promoters, SCN2A and synapasin1.1. Thus, to assay for LSD1 activity in vivo, the change of H3K4Me2 state of the LSD1 target promoters after fluvastatin treatment were measured using the chromatin immunoprecipitation (ChIP) assay. It was show that treatment of HeLa cells with 5 M fluvastatin caused a 30% increase in H3K4Me2 levels on the SCN2A promoter and a 90% increase in H3K4Me2 levels on the synapasin1.1 gene promoter as compared to vehicle alone (FIG. 4A, columns 2). Similar increases in H3K4Me2 levels of SCN2A and syn1-1 were observed when LSD1 activity was reduced through the use of LSD1 siRNA (16). Importantly, in the presence of fluvastatin, the levels of LSD1 enzyme bound to the SCN2A and synapasin1.1 promoters did not change, indicating that the increased level of H3K4 dimethylation was due to the inhibition of LSD1 H3K4Me2 demethylase activity and not to changes in association of LSD1 protein with the promoters (FIG. 4A, columns 3). These findings are consistent with our hypothesis that statins inhibit LSD1 activity in vivo.

Because LSD1 is a co-repressor silencing transcription of SCN2A and syn1.1, and these transcriptional effects are largely dependent on LSD1's H3K4Me2 demethylase activity, it was hypothesized that statins would increase expression of LSD1-responsive genes. As shown in FIG. 4B, treatment with fluvastatin (square), lovastatin (circle), and simvastatin (diamond) resulted in significant increases in mRNA levels of SCN2A and syn1.1. The effectiveness of statins in increasing gene expression was in the order of fluvastatin>lovastatin>simvastatin, corresponding to the same order of their inhibitory effect on LSD1 activity in vitro. Pravastatin did not show an effect of on gene expression (FIG. 4B), consistent with our finding that pravastatin did not inhibit LSD1 demethylase activity in vitro.

These data strongly indicate that statins inhibit LSD1 repression of gene expression by reducing LSD1 enzymatic activity. If so, increasing the levels of LSD1 protein should saturate the specific statins and overcome their effect on LSD1 target genes. To test this hypothesis, we established a stable HeLa cell line that over-expresses Flag-tagged full-length LSD1 (FgLSD1) at levels roughly 100-fold of that of mock transfected control cells. Transcript levels of the LSD1 target genes, a prototype target syn1.1 and a recently identified target IL-6 (32), were assessed in mock and FgLSD1 over-expressing cells treated with or without fluvastatin, lovastatin or pravastatin. As demonstrated above, fluvastatin and lovastatin caused similar increases in syn1.1 expression in mock control cells, while these effects were markedly blunted in the FgLSD1 cells overexpressing LSD1 (FIG. 4C). Again, pravastatin did not affect expression of the LSD1 target genes in either control or LSD1-overexpressed cells. Thus, overexpressing LSD1 overcomes the ability of statins to regulate expression of LSD1 target genes, lending further support to the hypothesis that LSD1 is a specific cellular target of a subtype of statins.

Figure 5A:
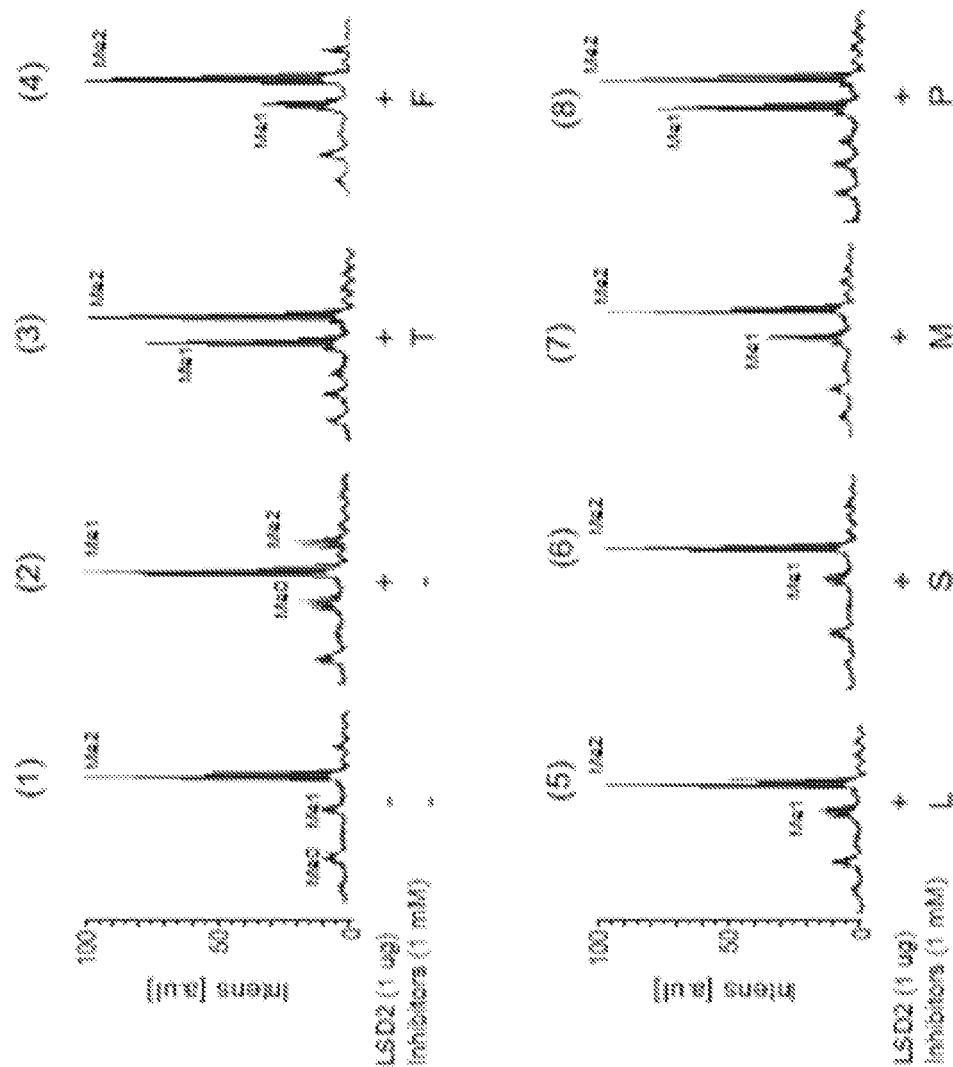

Statins inhibit the demethylase activity of LSD2 toward specific histone mark. By using multiple independent approaches as stated above to demonstrate the inhibitory effect of statins on LSD1, employed similar approach was also to study the statin effect on LSD2 enzymatic activity at biochemical, cellular, and molecular biological levels. As it has been previously reported that the enzymatic activity of LSD2 can be readily detected by Mass Spectrometry, using synthetic H3K4Me2 peptide as substrate [24]. In contrast to LSD1, recombinant LSD2 enzyme can decrease the 2864 Da peak and result in the generation of only one new peak, 2850 Da (Me1) as the expected demethylation products monoMeK4H3 (Me1). No unmodified histone H3 peptide (Me0) was detected (FIG. 5A). The data indicated that all the statins except pravastatin have better inhibitory effects than tranylcypromine, which has been reported as an LSD1 inhibitor with LSD2 inhibition function (FIG. 5A). Moreover, increasing the concentration of fluvastatin from 0 to 1000 M) resulted in a dose-dependent inhibition of LSD2 activity, as manifested by the decrease in the demethylation products H3K4Me1 and a corresponding increase in the H3K4Me2 substrate (FIG. 5B). LSD2 demethylase assay was also performed using an antibody that specifically recognizes H3K4Me2 on bulk histones. Consistent with the peptide/MALDI-TOF mass spectrometry assay results, fluvastatin inhibited LSD2 demethylase activity on bulk histones in a dose-dependent manner (FIG. 5C). These data demonstrate that a subset of statins act as inhibitors of the histone demethylase LSD2 in vitro and in vivo, indicating that histone demethylase LSD2 is also a novel cellular target of statins.

Figure 6A:
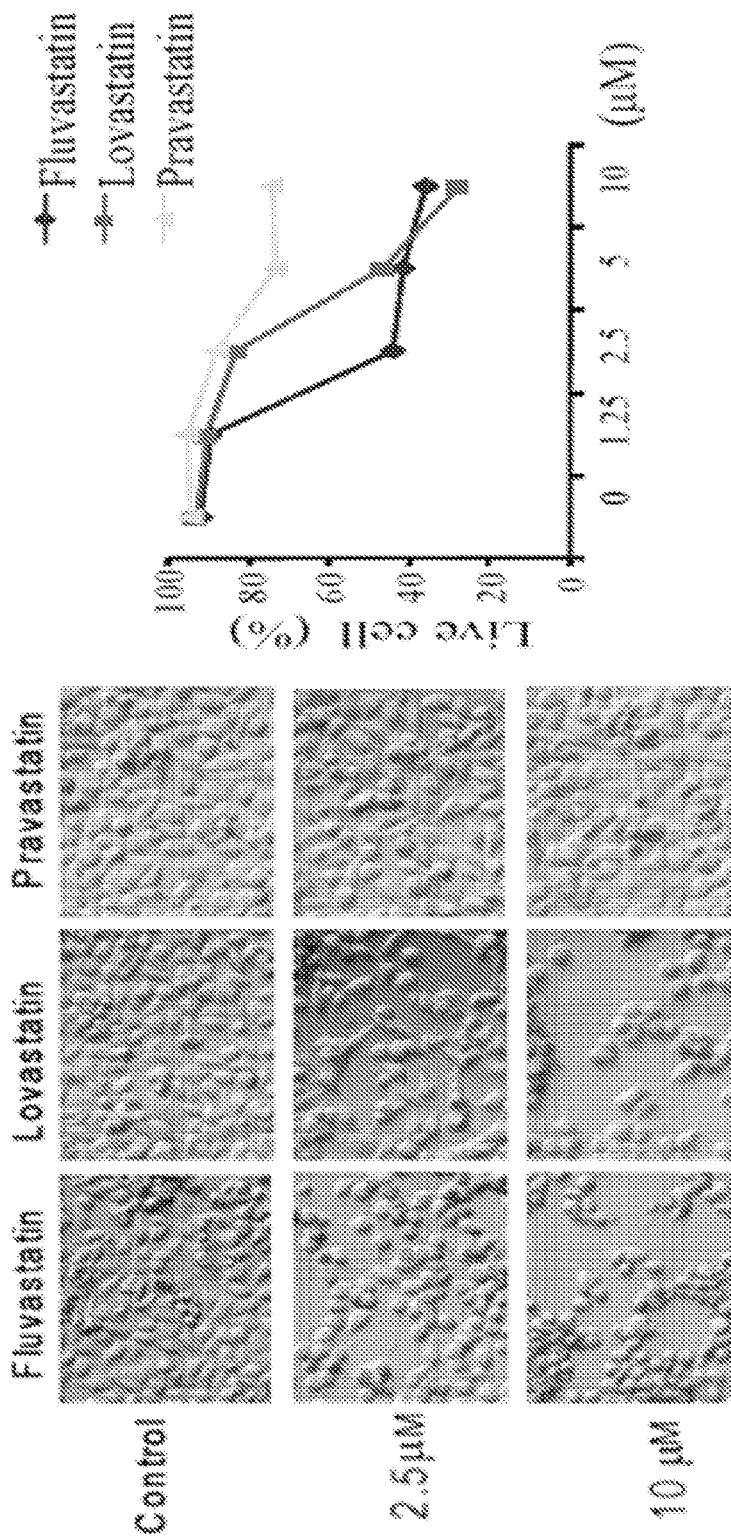
FIG. 6A-6C show that statin induce apoptosis in cancer cells mediated by LSD1 and LSD2.
Figure 6B:
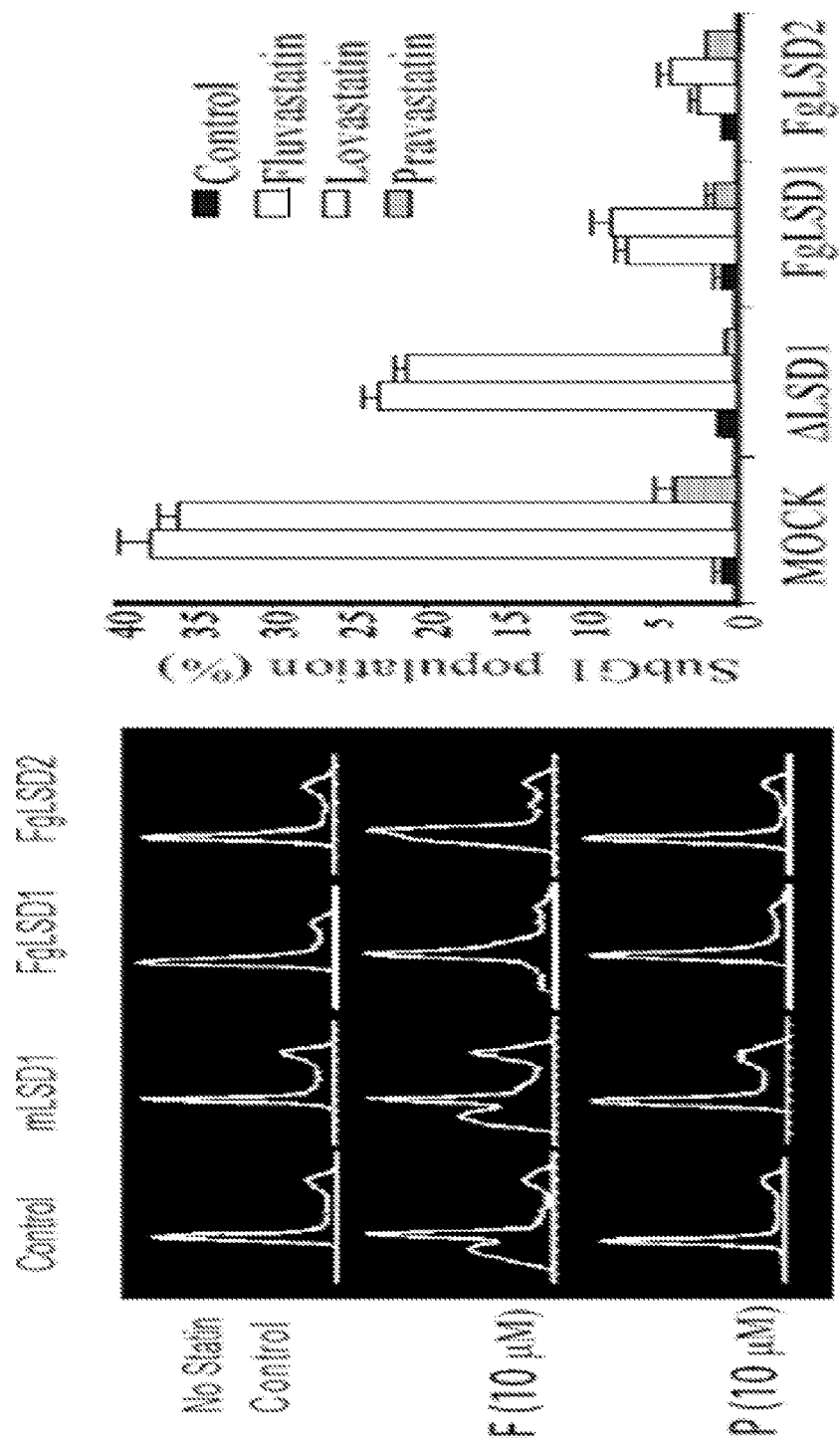

Overexpression LSD1 and LSD2 rescue statin-induced cell death in human cancer cells independent of mevalonate biosynthesis pathway. The anti-proliferative effect of statins in Hela cells in vitro was next tested that by treating them with various doses of fluvastatin, lovastatin and pravastatin for 24 hours. Fluvastatin and lovastatin induced cell death at concentrations of 2.5-5 µM. There was no significant cell death with pravastatin treatment at concentrations less than 10 µM (FIG. 6A). Furthermore, by flow cytometry, fluvastatin and lovastatin induced a large subG1 population in POZ cells stably expressed with control vector and the mutant LSD1. In comparison, cells overexpressing LSD1 and CTBP, a cellular repressor complex that contains LSD1, showed a markedly decrease of subG1 population (FIG. 6B). LSD1 POZ had two hundred-fold higher expression of LSD1 comparing with the control MOCK and mutant LSD1 POZ cells (data not shown). Consistent with literature, treatment with pravastatin had a smaller effect compared to that of fluvastatin and lovastatin.

Figure 7:
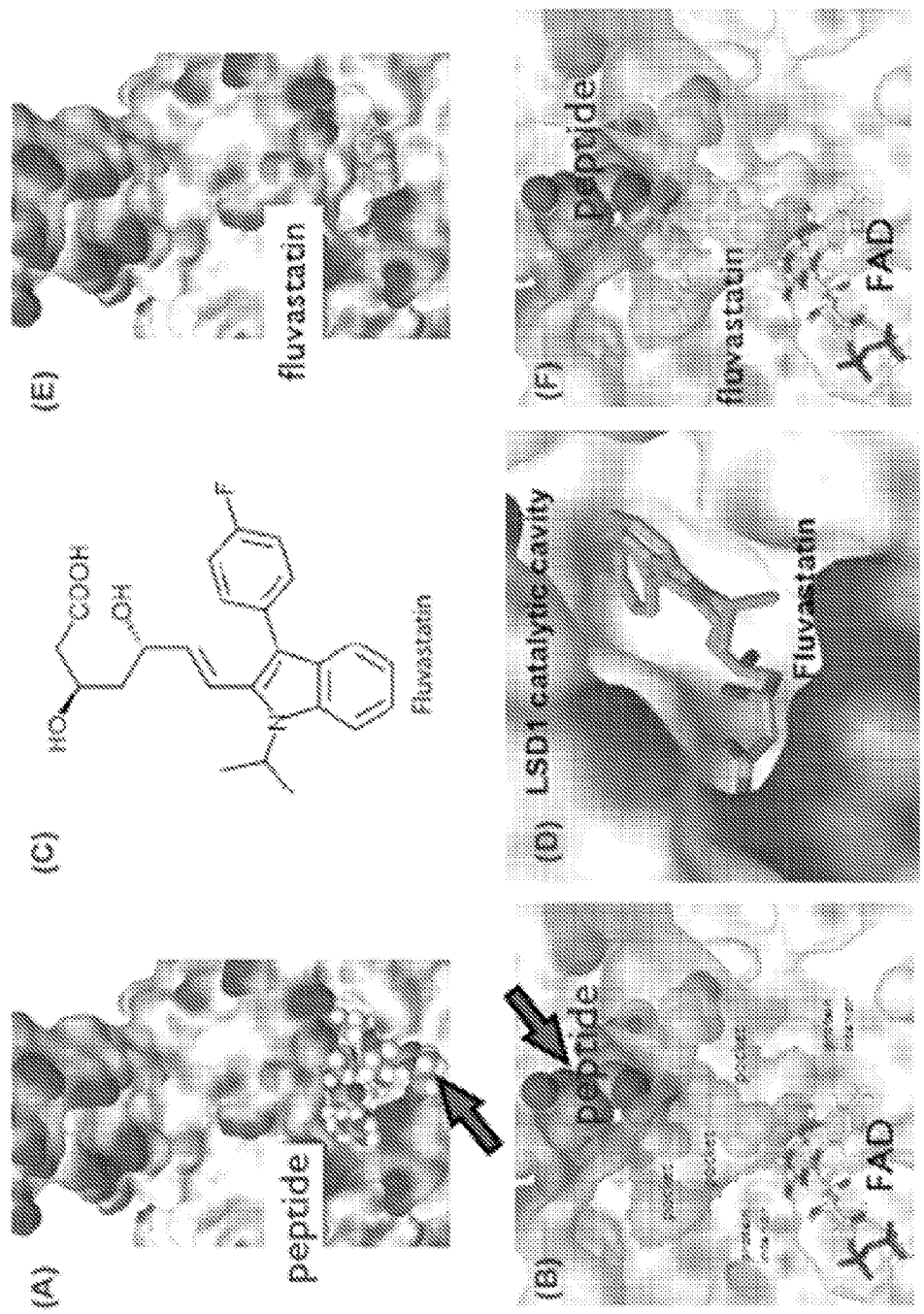
FIGS. 7A-7F show the predicted structures of LSD1 and fluvastatin, and a novel model for the cellular and physiological effect of the statin-LSD1 interaction.

A subset of statin molecules fit into the catalytic domain of the LSD1 and inhibit its catalytic activity. To gain insight into the extent to which statin molecules could fit into the catalytic domain of LSD1 and inhibit its catalytic activity, we next explored the relationship between LSD1 protein and statins at the level of atomic structure using a systematic computational docking program, Maestro/Glide/Ligprep (Schrödinger's computational technology, Schrödinger LLC) (FIG. 7). The full docking set, which consisted of the five representative statins used in this study and over one thousand randomly chosen chemical compounds from a decoy set, was used for a no-bias best-fit evaluation. Consistent with our findings, the highest scoring statin was fluvastatin (score of −10.17), ranking number 18 among the full docking set. Importantly, in the simulated co-structure of LSD1/fluvastatin complex, the fluorophenyl group of fluvastatin packs tightly against the FAD portion of the LSD1 demethylase catalytic cavity (FIG. 7B), with the fluorine atom (FIG. 7C, letter F in insert A' and green on fluorophenyl group) pointing towards the positively-charged patch created by Lys 661. We also superimposed the fluvastatin molecule into the catalytic cavity of the LSD1 demethylase in the presence of the putative substrate (FIG. 7D). This model indicates that by physically occupying the catalytic pocket, statins can prevent the docking and positioning of methylated substrates in the catalytic cavity, thus inhibiting substrate catalysis, and the fluorophenyl group of fluvastatin may be important for its inhibitory effect on LSD1. Taken together, this computer docking and modeling analysis provides a structural rationale for the inhibition of LSD1 by statins.

There is growing awareness from recent clinical data that statins may have anti-tumor effects in various types of cancer. In melanoma, the Air Force/Texas Coronary Atherosclerosis Prevention Study (AFCAPS/TexCAPS) evaluation of the efficacy of lovastatin in preventing coronary events found a significant decreased incidence of new melanomas in the lovastatin group [56]. In addition, the Veterans Affairs Cooperative Studies Program High-Density Lipoprotein Cholesterol Intervention Trial [VA-HIT]demonstrated a significant reduction in melanoma with gemfibrozil treatment [57]. A number of translational studies that have investigated the effects of statins on melanoma cells showed them to induce apoptosis, reduce tumor growth, and diminish angiogenesis, [58], [59]. Moreover, statins have been shown to heighten the response to chemotherapy drugs in the B16 mouse model of melanoma [60]. Lung cancer incidence rates in statin users were found to be significantly reduced (55% risk reduction) in the Veterans Affairs (VA) Health Care System case control study [12]. Overall, statin use also has been reported was associated with a risk reduction of human cancers of 20% (adjusted odds ratio [OR], 0.80; 95% CI, 0.66 to 0.96) [61]. However, other studies have shown no anti-cancer benefit for statins. A meta-analysis study including 6662 incident cancers and 2407 cancer deaths showed that statins did not reduce the incidence of cancer (OR, 1.02; 95% CI, 0.97-1.07) or cancer deaths (OR, 1.01; 95% CI, 0.93-1.09), and there was no reduction in any individual cancer type [62]. Two studies reported that there were no benefits with statin treatment in breast cancer [63-64], although other clinical and translational/basic research data support beneficial effects in breast cancer [14], [65]. These conflicting reports underscore the need to better understand the effects of statins in cancer biology.

Figure 6C:
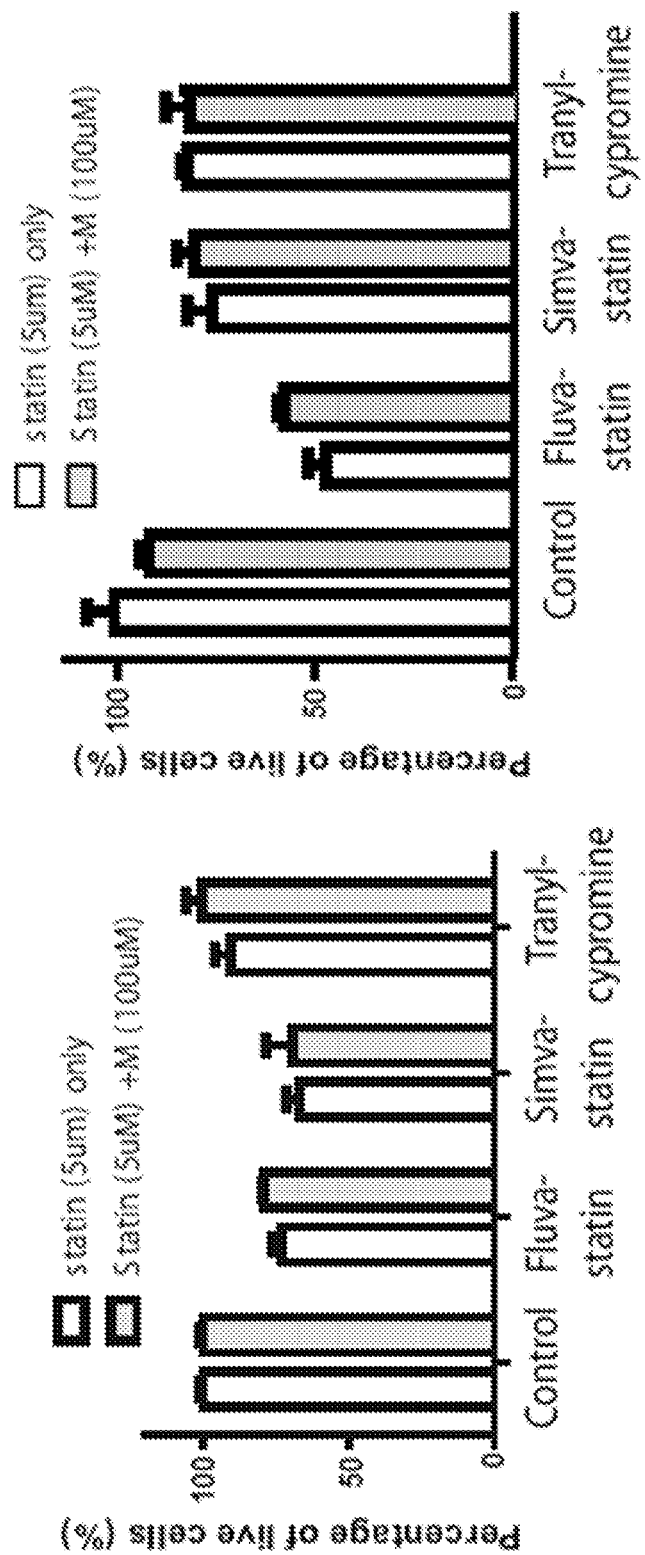

The current findings indicate an epigenetic mechanism for anti-tumor effects of statins involving inhibition of histone demethylases, which could provide new insights to the conflicting data from clinical trials. First, it is well established that the distribution of histone demethylase expression is tissue-specific, and different cancers have different profiles of histone demethylase expression. From the AFCAPS data, melanoma was the only type of cancer with significant beneficial effect (p<0.004), while all the other types of cancer in that study derived no benefits from the same statin regimen [66]. LSD2 expression was significantly higher in human breast cancer cells (data not shown) MDA231 comparing to MCF7 cell lines (data not shown) and human melanoma cell line WM793 comparing to WM1205 (data not shown). Moreover, LSD2 can be detected in a subset of tumor cells in melanoma by IHC. IHC staining with anti-LSD2 antibody in melanoma tissue sections showed strong positivity in a subset of tumor cells (data not shown). The data in the present study demonstrate breast cancer and melanoma cell lines have different expression levels of LSD2. In addition, to achieve the same efficacy of statin treatment, different cancer cells require different dosages of statins in vitro (FIG. 2). Thus, clinical trials with the same dose of statins should have different efficacies with respect to variations in cancer types with different levels of histone demethylase expressions levels and growth characteristics. Also potentially relevant is the recent proposal that cancer stem cells arise through epigenetic changes [67]. Emerging data have shown cancer stem cells have high expression levels of histone demethylases in various cancers, including lysine demethylase 5 KDM5/JARID1 in melanoma [68], [69], GASC1 histone demethylase as a driving oncogene in the 9p23-24 amplicon in human breast cancer [70], KDM2b/JHDM1b in acute myeloid leukemia [71], and KDM6b in Hodgkin's lymphoma [72]. Also, it has been reported that LSD1 overexpression contributes to human carcinogeneses through chromatin regulation in various cancers [42, 73-74] and regulates microenvironment niches for stem cells [75]. Accordingly, different tumors at different stages with different percentages of cancer stem cell populations with different histone demethylase expression profiles will affect efficacy of statin and other chemo-therapy. Moreover, use of LSD1 inhibitors combined with HDAC inhibitors synergistically enhances apoptotic cell death in breast cancer and glioblastoma multiforme cells [50-51]. These reports make histone demethylases attractive therapeutic targets in cancer. The current data are consistent with reports in the literature that statins can induce tumor cell apoptosis in HeLa cells and breast cancer and melanoma cells in culture (FIG. 6).

To exclude the possibility that the changes in H3K4Me2 dimethylation and expression of LSD target genes was due to inhibition of HMG-CoA reductase by statins, the cultured cancer cells and HeLa cells were supplied with mevalonate, the product of HMG-CoA reductase catalyzed reaction, to allow the cells to by-pass the requirement for HMG-CoA reductase activity. The addition of mevalonate did not rescue the cell death of cancer cells in breast cancer and melanoma; moreover, mevalonate did not reverse the derepression of the LSD1 target genes by statins (FIG. 4D). The data here indicate that the genomic pathway of statins involving histone demethylases as cellular targets plays a critical role in the anti-tumor effect of statins by targeting at cancer stem cells and tumor cells resistant to chemotherapy, while non-genomic HMG-CoA reductase pathway of statins play more important role in lipid-lowing effect of statins.

Different statins have different effects on inhibiting LSD1/2, and only a subset of statins can inhibit histone demethylases. The data here show that pravastatin cannot inhibit LSD1 and LSD2 by multiple independent experiments in vitro, including mass spec and demethylation assays (FIG. 1 and FIG. 5). Furthermore, pravastatin did not induce apoptosis in cultured HeLa cells in vivo (FIG. 6). This may provide insight to the results of the two clinical trials showing statins have no benefits in breast cancer patients, since both trials used pravastatin. Thus, the current study of identifying histone demethylase as cellular targets of statins provided insight on the understanding of anti-cancer effect of statins It provides new information to the future better design of clinical trial and potential clinical application of statins in cancer treatment. Moreover, statins as novel LSD inhibitors can be clinically used as adjuvant therapeutic agents to cancer treatment given the few side effects and low cost.

Figure 8:
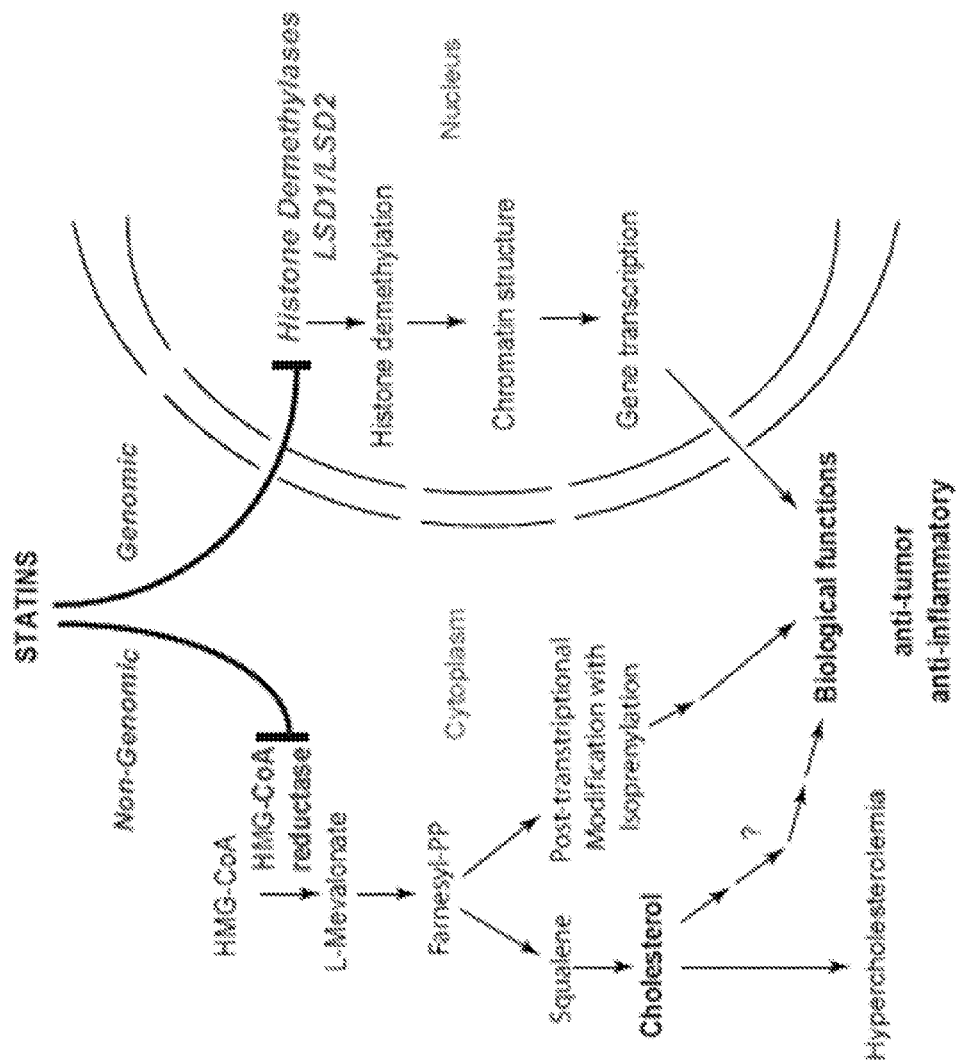
FIG. 8 shows a new model for the cellular effect of statins. Statins may influence the cellular activity or human physiology through two pathways. Left: well-characterized inhibition of HMG-CoA reductase (non-genomic pathway); Right, a previously unrecognized genomic pathway, i.e. statin-mediated LSD1 inhibition and resultant gene regulation, is represented. Both pathways intersect to effect common biological functions.

Using multiple independent approaches, it was shown that a subset of statins act as inhibitors of the histone demethylases LSD1 and LSD2, indicating that histone demethylases are cellular targets of statins. Importantly, inactivation of LSD1 by a subset of statins at a cellular level not only results in histone code changes in the LSD1 target genes but also consequently reprograms the expression of the target genes: statins are capable of de-repressing a subsets of neuronal specific genes, such as SCN2A and synapsin 1.1, and pro-inflammatory genes, such as IL-6 genes in non-neuronal HeLa cells. Thus, in addition to the well-established lipid-related pathways (non-genomic), the findings here indicate a new pathway (genomic), in which statins inhibit a key enzyme in the epigenetic gene regulation of many important biological functions and pathological processes (FIG. 8).

Example 2

Drug Screening Using a Melanoma Model in a Zebrafish Melanoma Model

The miniCoopR assay was performed as previously described (Ceol et al., 2011). Briefly, transgenes were expressed in zebrafish melanocytes in the background of a stably-integrated BRAFV600E transgene and a p53 loss-of-function mutation. The background also contained a mitfa loss-offunction mutation, which blocked melanocyte development. Transgenes were coupled, via the miniCoopR vector, to a rescuing mitfa gene, ensuring that rescued melanocytes also expressed the transgene being tested. Then different type of statins with different doses will be administered to the melanoma forming zebrafish. Then drug effects will be monitored and scored by melanomas formations in zebrasfish. When the animals are sacrificed, tumors will be formalin fixed, embedded and sectioned transversely to be assessed.

The references and patent applications cited herein and throughout the specification are incorporated herein by reference in their entirety.

REFERENCES

1. Alberts, A. W., Discovery, biochemistry and biology of lovastatin. Am J Cardiol, 1988. 62(15): p. 10J-15J.
2. Istvan, E. S. and J. Deisenhofer, Structural mechanism for statin inhibition of HMG-CoA reductase. Science, 2001. 292(5519): p. 1160-4.
3. Carroll, M. D., et al., Trends in serum lipids and lipoproteins of adults, 1960-2002. Jama, 2005. 294(14): p. 1773-81.
4. Cannon, C. P., et al., Intensive versus moderate lipid lowering with statins after acute coronary syndromes. N Engl J Med, 2004. 350(15): p. 1495-504.
5. Baigent, C., et al., Efficacy and safety of cholesterol-lowering treatment: prospective meta-analysis of data from 90,056 participants in 14 randomised trials of statins. Lancet, 2005. 366(9493): p. 1267-78.
6. Ridker, P. M., et al., C-reactive protein levels and outcomes after statin therapy. N Engl J Med, 2005. 352(1): p. 20-8.
7. Leung, B. P., et al., A novel anti-inflammatory role for simvastatin in inflammatory arthritis. Immunol, 2003. 170 (3): p. 1524-30.
8. Kronmann, L., C. Hatfield, and K. Kronmann, Statin therapy: not just used to lower cholesterol? Crit. Care Nurs Q, 2007. 30(2): p. 154-60.
9. Kaushal, V., et al., Potential anticancer effects of statins: fact or fiction? Endothelium, 2003. 10(1): p. 49-58.
10. Liao, J. K. and U. Laufs, Pleiotropic effects of statins. Annu Rev Pharmacol Toxicol, 2005. 45: p. 89-118.
11. Poynter, J. N., et al., Statins and the risk of colorectal cancer. N Engl J Med, 2005. 352(21): p. 2184-92.
12. Khurana, V., et al., Statins reduce the risk of lung cancer in humans: a large case-control study of US veterans. Chest, 2007. 131(5): p. 1282-8.
13. Wong, W. W., et al., HMG-CoA reductase inhibitors and the malignant cell: the statin family of drugs as triggers of tumor-specific apoptosis. Leukemia, 2002. 16(4): p. 508-19.
14. Campbell, M. J., et al., Breast cancer growth prevention by statins. Cancer Res, 2006. 66(17): p. 8707-14.
15. Cicha, I., et al., Monitoring the cellular effects of HMG-CoA reductase inhibitors in vitro and ex vivo. Arterioscler Thromb Vasc Biol, 2004. 24(11): p. 2046-50.
16. Takemoto, M., et al., Rho-kinase mediates hypoxia-induced downregulation of endothelial nitric oxide synthase. Circulation, 2002. 106(1): p. 57-62.
17. Maack, C., et al., Oxygen free radical release in human failing myocardium is associated with increased activity of rac1-GTPase and represents a target for statin treatment. Circulation, 2003. 108(13): p. 1567-74.
18. Barclay, M., et al., Human plasma lipoproteins, I. In normal women and in women with advanced carcinoma of the breast. Cancer, 1955. 8(2): p. 253-60.
19. Kaufman, R. J., et al., Human plasma lipoproteins. II. The effect of osseous metastases in patients with advanced carcinoma of the breast. Cancer, 1955. 8(5): p. 888-9.
20. Ross, J. S., et al., Atherosclerosis and cancer: common molecular pathways of disease development and progression. Ann N Y Acad Sci, 2001. 947: p. 271-92; discussion 292-3.
21. Mahadevan, N. R., et al., Transmission of endoplasmic reticulum stress and pro-inflammation from tumor cells to myeloid cells. Proc Natl Acad Sci USA, 2011. 108(16): p. 6561-6.
22. Lan, F., A. C. Nottke, and Y. Shi, Mechanisms involved in the regulation of histone lysine demethylases. Curr Opin Cell Biol, 2008. 20(3): p. 316-25.
23. Karytinos, A., et al., A novel mammalian flavin-dependent histone demethylase. J Biol Chem, 2009. 284(26): p. 17775-82.
24. Fang, R., et al., Human LSD2/KDM1b/AOF1 regulates gene transcription by modulating intragenic H3K4me2 methylation. Mol Cell, 2010. 39(2): p. 222-33.
25. Abdolmaleky, H. M., et al., Hypermethylation of the reelin (RELN) promoter in the brain of schizophrenic patients: a preliminary report. Am J Med Genet B Neuropsychiatr Genet, 2005. 134(1): p. 60-6.
26. Metzger, E., et al., LSD1 demethylates repressive histone marks to promote androgen-receptor-dependent transcription. Nature, 2005. 437(7057): p. 436-9.
27. Tzschach, A., et al., Novel JARID1C/SMCX mutations in patients with X-linked mental retardation. Hum Mutat, 2006. 27(4): p. 389.
28. Schmidt, D. M. and D. G. McCafferty, trans-2-Phenylcyclopropylamine is a mechanism-based inactivator of the histone demethylase LSD1. Biochemistry, 2007. 46(14): p. 4408-16.
29. Rosendorff, A., et al., NXP-2 association with SUMO-2 depends on lysines required for transcriptional repression. Proc Natl Acad Sci USA, 2006. 103(14): p. 5308-13.
30. Formeris, F., et al., Human histone demethylase LSD1 reads the histone code. J Biol Chem, 2005. 280(50): p. 41360-5.
31. Gamble, M. J. and W. L. Kraus, Visualizing the histone code on LSD1. Cell, 2007. 128(3): p. 433-4.

32. Di Stefano, L., et al., Mutation of Drosophila Lsd1 disrupts H3-K4 methylation, resulting in tissue-specific defects during development. Curr Biol, 2007. 17(9): p. 808-12.
33. Abidi, F. E., et al., A novel mutation in the PHF8 gene is associated with X-linked mental retardation with cleft lip/cleft palate. Clin Genet, 2007. 72(1): p. 19-22.
34. Chosed, R. and S. Y. Dent, A two-way street: LSD1 regulates chromatin boundary formation in S. pombe and Drosophila. Mol Cell, 2007. 26(2): p. 160-2.
35. Saleque, S., et al., Epigenetic regulation of hematopoietic differentiation by Gfi-1 and Gfi-1b is mediated by the cofactors CoREST and LSD1. Mol Cell, 2007. 27(4): p. 562-72.
36. Wang, J., et al., Opposing LSD1 complexes function in developmental gene activation and repression programmes. Nature, 2007. 446(7138): p. 882-7.
37. Barski, A., et al., High-resolution profiling of histone methylations in the human genome. Cell, 2007. 129(4): p. 823-37.
38. Kahl, P., et al., Androgen receptor coactivators lysine-specific histone demethylase 1 and four and a half LIM domain protein 2 predict risk of prostate cancer recurrence. Cancer Res, 2006. 66(23): p. 11341-7.
39. Huang, J., et al., p53 is regulated by the lysine demethylase LSD1. Nature, 2007. 449(7158): p. 105-8.
40. Chau, C. M., et al., Cell cycle association of the retinoblastoma protein Rb and the histone demethylase LSD1 with the Epstein-Barr virus latency promoter Cp. J Virol, 2008. 82(7): p. 3428-37.
41. Wang, J., et al., The lysine demethylase LSD1 (KDM1) is required for maintenance of global DNA methylation. Nat Genet, 2009. 41(1): p. 125-9.
42. Hayami, S., et al., Overexpression of LSD1 contributes to human carcinogenesis through chromatin regulation in various cancers. Int J Cancer, 2011. 128(3): p. 574-86.
43. Heidenblad, M., et al., Tiling resolution array CGH and high density expression profiling of urothelial carcinomas delineate genomic amplicons and candidate target genes specific for advanced tumors. BMC Med Genomics, 2008. 1: p. 3.
44. Orlic, M., et al., Expression analysis of 6p22 genomic gain in retinoblastoma. Genes Chromosomes Cancer, 2006. 45(1): p. 72-82.
45. Szewczuk, L. M., et al., Mechanistic analysis of a suicide inactivator of histone demethylase LSD1. Biochemistry, 2007. 46(23): p. 6892-902.
46. Culhane, J. C. and P. A. Cole, LSD1 and the chemistry of histone demethylation. Curr Opin Chem Biol, 2007.
47. Formeris, F., et al., LSD1: oxidative chemistry for multifaceted functions in chromatin regulation. Trends Biochem Sci, 2008. 33(4): p. 181-9.
48. Rudolph, T., et al., Heterochromatin formation in Drosophila is initiated through active removal of H3K4 methylation by the LSD1 homolog SU(VAR)3-3. Mol Cell, 2007. 26(1): p. 103-15.
49. Argentaro, A., et al., Structural consequences of disease-causing mutations in the ATRX-DNMT3-DNMT3L (ADD) domain of the chromatin-associated protein ATRX. Proc Natl Acad Sci USA, 2007. 104(29): p. 11939-44.
50. Huang, Y., et al., Inhibitors of histone demethylation and histone deacetylation cooperate in regulating gene expression and inhibiting growth in human breast cancer cells. Breast Cancer Res Treat, 2011.
51. Singh, M. M., et al., Inhibition of LSD1 sensitizes glioblastoma cells to histone deacetylase inhibitors. Neuro Oncol, 2011. 13(8): p. 894-903.
52. Benelkebir, H., et al., Enantioselective synthesis of tranylcypromine analogues as lysine demethylase (LSD1) inhibitors. Bioorg Med Chem, 2011. 19(12): p. 3709-16.
53. Sharma, S. K., et al., (Bis)urea and (bis)thiourea inhibitors of lysine-specific demethylase 1 as epigenetic modulators. J Med Chem, 2010. 53(14): p. 5197-212.
54. Binda, C., et al., Biochemical, structural, and biological evaluation of tranylcypromine derivatives as inhibitors of histone demethylases LSD1 and LSD2. J Am Chem Soc, 2010. 132(19): p. 6827-33.
55. Lizcano, J. M., M. Unzeta, and K. F. Tipton, A spectrophotometric method for determining the oxidative deamination of methylamine by the amine oxidases. Anal Biochem, 2000. 286(1): p. 75-9.
56. Downs, J. R., et al., Primary prevention of acute coronary events with lovastatin in men and women with average cholesterol levels: results of AFCAPS/TexCAPS. Air Force/Texas Coronary Atherosclerosis Prevention Study. JAMA, 1998. 279(20): p. 1615-22.
57. Rubins, H. B., et al., Gemfibrozil for the secondary prevention of coronary heart disease in men with low levels of high-density lipoprotein cholesterol. Veterans Affairs High-Density Lipoprotein Cholesterol Intervention Trial Study Group. N Engl J Med, 1999. 341(6): p. 410-8.
58. Shellman, Y. G., et al., Lovastatin-induced apoptosis in human melanoma cell lines. Melanoma Res, 2005. 15(2): p. 83-9.
59. Depasquale, I. and D. N. Wheatley, Action of Lovastatin (Mevinolin) on an in vitro model of angiogenesis and its co-culture with malignant melanoma cell lines. Cancer Cell Int, 2006. 6: p. 9.
60. Feleszko, W., et al., Potentiated antitumour effects of cisplatin and lovastatin against MmB16 melanoma in mice. Eur J Cancer, 1998. 34(3): p. 406-11.
61. Graaf, M. R., et al., The risk of cancer in users of statins. J Clin Oncol, 2004. 22(12): p. 2388-94.
62. Dale, K. M., et al., Statins and cancer risk: a meta-analysis. JAMA, 2006. 295(1): p. 74-80.
63. Woditschka, S., et al., Lipophilic statin use and risk of breast cancer subtypes. Cancer Epidemiol Biomarkers Prev, 2010. 19(10): p. 2479-87.
64. Lubet, R. A., et al., Lack of efficacy of the statins atorvastatin and lovastatin in rodent mammary carcinogenesis. Cancer Prev Res (Phila), 2009. 2(2): p. 161-7.
65. Shibata, M. A., et al., Lovastatin inhibits tumor growth and lung metastasis in mouse mammary carcinoma model: a p53-independent mitochondrial-mediated apoptotic mechanism. Carcinogenesis, 2004. 25(10): p. 1887-98.
66. Siekmeier, R., et al., Dose dependency of fluvastatin pharmacokinetics in serum determined by reversed phase HPLC. J Cardiovasc Pharmacol Ther, 2001. 6(2): p. 137-45.
67. Feinberg, A. P., R. Ohlsson, and S. Henikoff, The epigenetic progenitor origin of human cancer. Nat Rev Genet, 2006. 7(1): p. 21-33.
68. Roesch, A., et al., A temporarily distinct subpopulation of slow-cycling melanoma cells is required for continuous tumor growth. Cell, 2010. 141(4): p. 583-94.
69. Blair, L. P., et al., Epigenetic Regulation by Lysine Demethylase 5 (KDM5) Enzymes in Cancer. Cancers (Basel), 2011. 3(1): p. 1383-1404.
70. Liu, G., et al., Genomic amplification and oncogenic properties of the GASC1 histone demethylase gene in breast cancer. Oncogene, 2009. 28(50): p. 4491-500.

71. He, J., A. T. Nguyen, and Y. Zhang, KDM2b/JHDM1b, an H3K36me2-specific demethylase, is required for initiation and maintenance of acute myeloid leukemia. Blood, 2011. 117(14): p. 3869-80.
72. Anderton, J. A., et al., The H3K27me3 demethylase, KDM6B, is induced by Epstein-Barr virus and over-expressed in Hodgkin's Lymphoma. Oncogene, 2011. 30(17): p. 2037-43.
73. Lim, S., et al., Lysine-specific demethylase 1 (LSD1) is highly expressed in ER-negative breast cancers and a biomarker predicting aggressive biology. Carcinogenesis, 2010. 31(3): p. 512-20.
74. Cho, H. S., et al., Demethylation of RB regulator MYPT1 by histone demethylase LSD1 promotes cell cycle progression in cancer cells. Cancer Res, 2011. 71(3): p. 655-60.
75. Eliazer, S., N. A. Shalaby, and M. Buszczak, Loss of lysine-specific demethylase 1 nonautonomously causes stem cell tumors in the Drosophila ovary. Proc Natl Acad Sci USA, 2011. 108(17): p. 7064-9.

What is claimed:

1. A method for treating cancer in a subject comprising:
   (a) determining the expression level of a histone lysine specific demethylase 1 (LSD1) and/or a histone lysine specific demethylase 2 (LSD2) from a sample of cancer cells derived from a subject; and
   (b) administering to a subject a therapeutically effective amount of an epigenetic modulating adjuvant agent in conjunction with at least one chemotherapy when there is an increased expression of LSD1 and/or LSD2 in the cancer cells,
      wherein the epigenetic modulating adjuvant agent is a statin, and
      wherein the epigenetic modulating adjuvant agent promotes chemo-protection and reducing chemo-resistance.

2. The methods of claim 1, wherein the statin induces cell apoptosis that is not mitigated by the mevalonate pathway, the by-product of HMG-CoA reductase.

3. The methods of claim 1, wherein the statin is selected from the group consisting of fluvastatin, lovastatin, simvastatin, mevastatin, atorvastatin, and rosuvastatin.

4. The methods of claim 1, wherein the statin is administered by a route selected from the group consisting of: intravenous, intramuscular, subcutaneous, intradermal, topical, intraperitoneal, intrathecal, intrapleural, intrauterine, rectal, vaginal, intrasynovial, intraocular/periocular, intratumor, and parenteral administration.

5. The methods of claim 1, wherein the at least one chemotherapy is an alkylating chemotherapeutic drug.

* * * * *